(12) United States Patent
Rhu et al.

(10) Patent No.: US 11,364,463 B2
(45) Date of Patent: Jun. 21, 2022

(54) APPARATUS AND METHOD FOR RECOVERING EFFECTIVE RESOURCES INCLUDING NITROGEN AND PHOSPHORUS

(71) Applicant: BKT CO., LTD., Daejeon (KR)

(72) Inventors: Daehwan Rhu, Yeoju-si (KR); Jaemin Choi, Hwaseong-si (KR); Minki Jung, Daejeon (KR); Hojae Hwang, Sejong (KR); Seyeong Kim, Daejeon (KR); Ken Tasaki, Redondo Beach, CA (US)

( * ) Notice: Subject to any disclaimer, the term of this patent is extended or adjusted under 35 U.S.C. 154(b) by 0 days.

(21) Appl. No.: 17/294,646

(22) PCT Filed: Oct. 30, 2019

(86) PCT No.: PCT/KR2019/014416
§ 371 (c)(1),
(2) Date: May 17, 2021

(87) PCT Pub. No.: WO2020/105886
PCT Pub. Date: May 28, 2020

(65) Prior Publication Data
US 2021/0354072 A1   Nov. 18, 2021

(30) Foreign Application Priority Data

Nov. 21, 2018  (KR) .......................... 10-2018-0144450
Jul. 5, 2019   (KR) .......................... 10-2019-0081586

(51) Int. Cl.
*B01D 47/02*   (2006.01)
*C02F 9/00*    (2006.01)
(Continued)

(52) U.S. Cl.
CPC ................ *B01D 47/02* (2013.01); *C02F 9/00* (2013.01); *C02F 1/20* (2013.01); *C02F 3/308* (2013.01);
(Continued)

(58) Field of Classification Search
None
See application file for complete search history.

(56) References Cited

U.S. PATENT DOCUMENTS

| 4,971,776 A | 11/1990 | Van Royen et al. |
| 7,842,186 B2 | 11/2010 | Chung et al. |

(Continued)

FOREIGN PATENT DOCUMENTS

| JP | 2002-273489 A | 9/2002 |
| JP | 2007-061710 A | 3/2007 |

(Continued)

OTHER PUBLICATIONS

English Specification of JP2002-273489A.
(Continued)

*Primary Examiner* — Chester T Barry
(74) *Attorney, Agent, or Firm* — Antonio Ha & U.S. Patent, LLC

(57) ABSTRACT

Disclosed are an apparatus and a method for recovering effective resources including nitrogen and phosphorus. According to one aspect of the present embodiment, provided are an apparatus and a method for recovering effective resources, which efficiently recover resources such as methane, nitrogen, and phosphorus while minimizing the use of chemicals.

13 Claims, 17 Drawing Sheets

(51) Int. Cl.
  *C02F 1/20*    (2006.01)
  *C02F 3/30*    (2006.01)
  *C02F 101/10*  (2006.01)
  *C02F 101/16*  (2006.01)

(52) U.S. Cl.
  CPC .... *C02F 2101/105* (2013.01); *C02F 2101/16* (2013.01)

(56) References Cited

U.S. PATENT DOCUMENTS

| | | | | |
|---|---|---|---|---|
| 2002/0074287 | A1* | 6/2002 | Park | C02F 3/348 |
| | | | | 210/605 |
| 2003/0217968 | A1* | 11/2003 | Goel | C02F 3/1221 |
| | | | | 210/605 |
| 2005/0035059 | A1* | 2/2005 | Zhang | C02F 1/441 |
| | | | | 210/605 |
| 2016/0347630 | A1* | 12/2016 | Vanotti | B01D 21/01 |
| 2018/0370830 | A1* | 12/2018 | Fitch | B01D 61/145 |
| 2019/0144320 | A1* | 5/2019 | Nilsen | C02F 11/121 |
| | | | | 210/603 |
| 2019/0185357 | A1* | 6/2019 | Delahaye | C02F 11/04 |

FOREIGN PATENT DOCUMENTS

| | | |
|---|---|---|
| KR | 10-19960003150 | 3/1996 |
| KR | 10-2000-0019613 | 4/2000 |
| KR | 10-2003-0016358 | 2/2003 |
| KR | 10-2010-0012887 | 2/2010 |

OTHER PUBLICATIONS

English Specification of JP2007-061710A.
English Specification of 10-19960003150.
English Specification of 10-2010-0012887.
English Specification of 10-2000-0019613.
English Specification of 10-2003-0016358.
Sengupta, S. et al. "Nitrogen and Phosphorus Recovery from Wastewater", Curr Pollution Rep., vol. 1, pp. 155-166 (Aug. 20, 2015).
Moore, S. E. et al. "Sustainable Struvite Control Using Carbon Dioxide", J. Environ. Eng., vol. 144, pp. 1-9.
Jiang et al. "Evaluation of an integrated ammonia stripping, recovery, and biogas scrubbingm system for use with anaerobically digested dairy manure", Biosyst. Eng., vol. 119, pp. 117-126 (2014.).

* cited by examiner

APPARATUS AND METHOD FOR RECOVERING EFFECTIVE RESOURCES INCLUDING NITROGEN AND PHOSPHORUS

CROSS-REFERENCE TO RELATED APPLICATIONS

The instant patent application claims priority under 35 U.S.C. 119(a) to Korean Patent Application Nos. 10-2018-0144450 and 10-2019-0081586, filed on Nov. 21, 2018 and Jul. 5, 2019, respectively, in the Korean Intellectual Property Office, the disclosures of which are herein incorporated by reference in their entireties.

BACKGROUND OF THE INVENTION

Field of the Invention

The present invention relates to a device and method for recovering effective resources including nitrogen and phosphorus for organic waste.

Description of Related Art

The description of the Discussion of Related Art section merely provides information that may be relevant to embodiments of the disclosure but should not be appreciated as necessarily constituting the prior art.

Anaerobic digestion technology is a representative technology for reducing organic waste, such as livestock manure, food waste or sewage waste and is applied to public livestock manure treatment facilities, food recycling facilities, or sewage treatment facilities. Anaerobic digestion technology not only reduces organic waste but also recovers biogas containing 60% methane content and 40% carbon dioxide as by-products. Most of the digestate generated through anaerobic digestion is transferred to a sewage treatment facility and processed but, because of containing high concentrations of nitrogen and phosphorus, puts a burden on the water treatment process.

To address this problem, a purification facility removes nitrogen and phosphorus by performing a purification treatment so as to partially mitigate the burden on the water treatment process, but a large amount of money is required for the construction and maintenance for the facility.

For example, phosphorus in livestock manure exists bound with organic matter or while forming chemical bonds with various ions. To recover phosphorus, a conventional method is to elute phosphorus bound with organic matter and then precipitate struvite bound with magnesium and ammonia. However, a low pH needs to be formed to elute phosphorus bound with organic matter and other ions. To form a low pH, a strong acid solution, such as sulfuric acid or hydrochloric acid, needs be injected. However, since a large amount of strong acid solution needs to be consumed due to the high alkalinity of the digestion waste of livestock manure, the elution of phosphorus costs a lot.

Further, in the case of livestock manure, calcium ($CaHCO_3$), the main component of milk, is used together with feed so as to increase milk production in livestock farms that raise dairy cows. For this reason, dairy cow manure has a high alkalinity of about 10,000 mg/L to 12,000 mg/L and a high calcium ion concentration ($Ca^{2}$). Further, in poultry farms, calcium is supplied to enhance the production and quality of eggs. In general, 4 g of calcium is supplied with feed to produce one egg. It is known that only 2 g, that is, 50%, of the calcium supplied with the feed is ingested and is used for egg production. For this reason, unused calcium and large amounts of carbonic acid ions ($HCO_3^{2-}$) are discharged along with poultry manure (chicken manure).

Domestic dairy cow farms generally use sawdust bedding barns that produce little cow manure. However, in the United States, a large amount of cow manure may be produced because scraping-type barns are used. In the United States, cow manure is introduced into an anaerobic digestion tank to produce biogas, and fiber is removed from the effluent while undergoing first solid-liquid separation and is recycled as bedding for livestock, and solids obtained through second solid-liquid separation is used as a compost material. When an anaerobic digestion tank is used to treat livestock manure, carbon (C) is recovered as methane ($CH_4$), but nitrogen and phosphorus are discharged in their entirety. In the United States, the discharged manure is injected into farmland for use in producing fodder crops, such as corn and soybeans. It is known that when nitrogen and phosphorus are continuously injected into farmland for a long period of time, unused nitrogen may move to the ground and contaminate groundwater, or phosphorus adsorbed in the soil may flow out along with rainwater, polluting rivers and lakes.

To solve these issues, organic waste is conventionally discharged after undergoing a purification process for removing and recovering nitrogen and phosphorus remaining in the organic waste. Although nitrogen may be mostly recovered by a denitrification process, phosphorus is not easy to recover. Phosphorus present in livestock manure is bound with organic matter or chemically bound with various ions, and more than 80% of it is present in a solid state. In particular, soluble phosphorus easily binds with calcium ions. In the case of dairy cow and poultry manure, since calcium ions are contained in large quantities, the amount of phosphorus present in a soluble state is considerably small. For this reason, since the solids in organic waste, along with a significant amount of phosphorus, are removed during a purification process, it is quite difficult to recover phosphorus by the conventional methods.

BRIEF SUMMARY OF THE INVENTION

An embodiment of the present invention aims to provide an effective resource recovery device and method for efficiently recovering resources, such as high-concentration methane gas, nitrogen, and phosphorus while minimizing the use of chemicals.

An embodiment of the present invention aims to provide an effective resource recovery device and method capable of economically recovering effective resources including nitrogen and phosphorus in organic waste through proper pretreatment and effective use of by-products.

According to an embodiment of the present invention, there is provided a device for recovering a resource contained in organic waste, comprising an anaerobic digester generating digestate and gases by performing anaerobic digestion on the organic waste; a solid-liquid separation tank separating the digestate into solid components and liquid components, an ammonia degassing tank degassing a part of ammonium ions into ammonia by injecting a predetermined amount of air into the liquid components separated in the solid-liquid separation tank, a gas-liquid dissolver receiving the gases and the ammonia, mixing the gases and the ammonia with dissolution water, dissolving a gas having a relatively high solubility in the dissolution water, and discharging a gas having a relatively low solubility in the dissolution water to an outside, a compound production unit providing a preset environment and producing a solid compound with a component dissolved in the dissolution water, an ion reactor receiving the liquid components passed through the ammonia degassing tank and an ion-binding material from the outside and producing a solid phosphate compound, and a recovery unit recovering the solid compound and the solid phosphate compound respectively produced in the compound production unit and the ion reactor.

According to an embodiment of the present invention, the ammonia degassing tank increases an ammonia degassing efficiency by injecting the preset amount of air to cause a pH rise, thereby degassing the ammonia.

According to an embodiment of the present invention, the gases include methane and carbon dioxide.

According to an embodiment of the present invention, the compound production unit produces ammonium bicarbonate using the carbon dioxide and the ammonia dissolved in the dissolution water.

According to an embodiment of the present invention, the recovery unit is connected to both the compound production unit and the ion reactor to simultaneously recover the solid compound and the solid phosphate compound or is separately connected to the compound production unit and the ion reactor to separately recover the solid compound and the solid phosphate compound.

According to an embodiment of the present invention, there is provided a method for recovering a resource contained in organic waste, comprising an anaerobic digestion step for generating digestate and gases by performing anaerobic digestion on the organic waste, a solid-liquid separation step for separating the digestate into solid components and liquid components, an ammonia degassing step for degassing a part of ammonium ions into ammonia by injecting a predetermined amount of air into the liquid components separated in the solid-liquid separation step, a gas-liquid dissolution step for receiving the gases and the ammonia, mixing the gases and the ammonia with dissolution water, dissolving a gas having a relatively high solubility in the dissolution water, and discharging a gas having a relatively low solubility in the dissolution water to an outside, a compound production step for producing a solid compound with a component dissolved in the dissolution water in a preset environment, an ion reaction step for receiving the liquid components passed through the ammonia degassing step and an ion-binding material from the outside and producing a solid phosphate compound, and a recovery step for recovering the solid compound and the solid phosphate compound respectively produced in the compound production step and the ion reaction step.

According to an embodiment of the present invention, there is provided a device for recovering a resource contained in organic waste, comprising an anaerobic digester decomposing the organic waste into digestate and gases by anaerobic digestion, a first solid-liquid separation tank separating the digestate into solid components and liquid components, an elution tank eluting a preset component among the solid components separated in the first solid-liquid separation tank, a second solid-liquid separation tank separating the component eluted through the elution tank and remaining solid components, a recovery tank depositing the preset component from the components separated in the second solid-liquid separation tank, an aerobic tank injecting a predetermined amount of air into the liquid components separated in the first solid-liquid separation tank to degas some of ammonium ions into ammonia and generating the predetermined component remaining in the liquid components into a solid, a nitrogen recovery tank recovering a nitrogen component from ammonia degassed in the aerobic tank, and a third solid-liquid separation tank separating the solid generated in the aerobic tank and the liquid components.

According to an embodiment of the present invention, the third solid-liquid separation tank transfers the separated solid to the first solid-liquid separation tank.

According to an embodiment of the present invention, the nitrogen recovery tank provides a preset environment to recover the ammonia degassed in the aerobic tank in a liquid phase.

According to an embodiment of the present invention, the nitrogen recovery tank receives carbon dioxide and recovers the ammonia degassed in the aerobic tank as a solid compound.

According to an embodiment of the present invention, there is provided a method for recovering a resource contained in organic waste, comprising a decomposition step for decomposing the organic waste into digestate and gases by anaerobic digestion, a first solid-liquid separation step for separating the digestate into solid components and liquid components, an elution step for eluting a preset component among the solid components separated in the first solid-liquid separation step, a second solid-liquid separation step for separating the component eluted in the elution step and remaining solid components, a deposition step for depositing the preset component from the components separated in the second solid-liquid separation step, a degassing step for injecting a predetermined amount of air into the liquid components separated in the first solid-liquid separation step to degas some of ammonium ions into ammonia and generating the predetermined component remaining in the liquid components into a solid, a recovery step for recovering a nitrogen component from ammonia degassed in the degassing step, and a third solid-liquid separation step for separating the solid generated through the degassing step and the liquid components.

As described above, according to an aspect of the present invention, there is an advantage of efficiently recovering various resources, such as methane gas, nitrogen, and phosphorus while minimizing the use of chemicals.

Further, according to an aspect of the present invention, there is an advantage of being able to efficiently recover various effective resources including nitrogen and phosphorus from organic waste while minimizing the use of chemicals by appropriate pretreatment and effective use of by-products.

DETAILED DESCRIPTION OF THE INVENTION

Various changes may be made to the present invention, and the present invention may come with a diversity of embodiments. Some embodiments of the present invention are shown and described in connection with the drawings. However, it should be appreciated that the present disclosure is not limited to the embodiments, and all changes and/or equivalents or replacements thereto also belong to the scope of the present disclosure. Similar reference denotations are used to refer to similar elements throughout the drawings.

The terms "first" and "second" may be used to describe various components, but the components should not be limited by the terms. The terms are used to distinguish one component from another. For example, a first component may be denoted a second component, and vice versa without departing from the scope of the present disclosure. The term "and/or" may denote a combination(s) of a plurality of related items as listed or any of the items.

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when a component is "directly connected to" or "directly coupled to" another component, no other intervening components may intervene therebetween.

The terms as used herein are provided merely to describe some embodiments thereof, but not to limit the present disclosure. As used herein, the singular forms "a," "an," and "the" are intended to include the plural forms as well, unless the context clearly indicates otherwise. As used herein, the term "comprise," "include," or "have" should be appreciated not to preclude the presence or addability of features, numbers, steps, operations, components, parts, or combinations thereof as set forth herein.

Unless otherwise defined, all terms including technical and scientific terms used herein have the same meaning as commonly understood by one of ordinary skill in the art to which the embodiments of the present disclosure belong.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The components, processes, steps, or methods according to embodiments of the disclosure may be shared as long as they do not technically conflict with each other.

Figure 1:
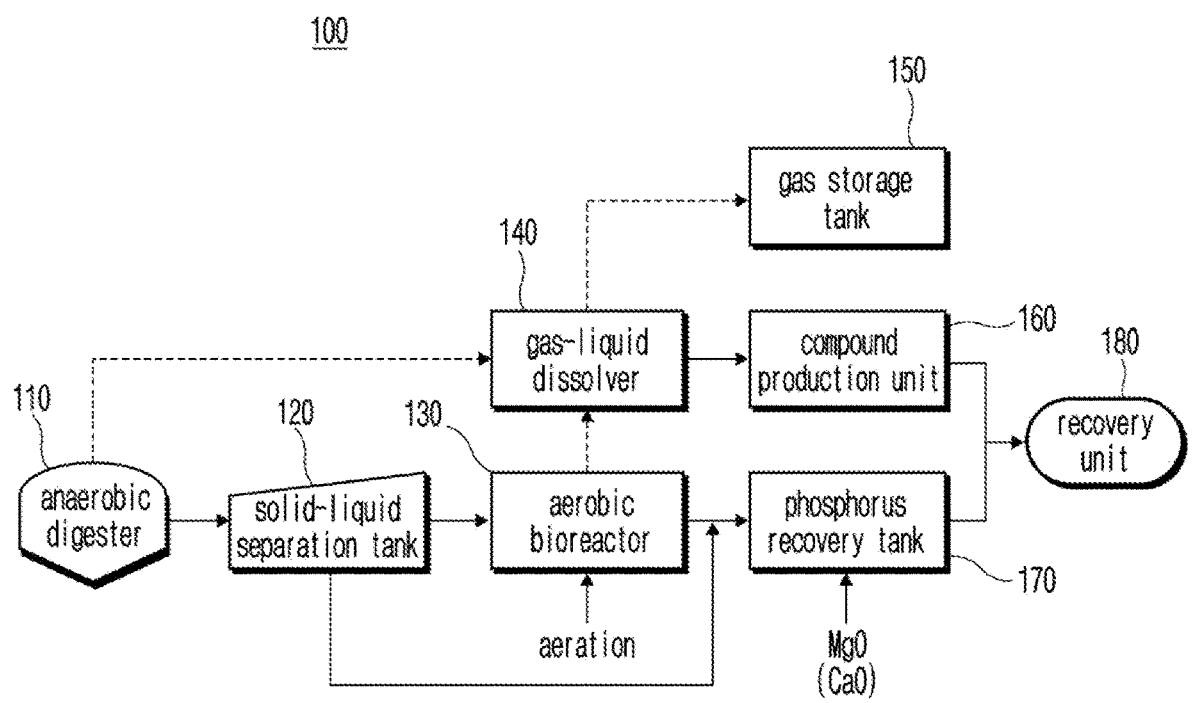
FIG. 1 is a view illustrating a configuration of an effective resource recovery device according to a first embodiment of the present invention.

FIG. 1 is a view illustrating a configuration of an effective resource recovery device according to a first embodiment of the present invention.

Referring to FIG. 1, an effective resource recovery device 100 according to a first embodiment of the present invention includes an anaerobic digester 110, a solid-liquid separation tank 120, an aerobic bioreactor (ammonia degassing tank, 130), a gas-liquid dissolver 140, a gas storage tank 150, a compound production unit 160, a phosphorus recovery tank (ion reactor, 170), and a recovery unit 180.

The anaerobic digester 110 decomposes organic waste into digestate and biogas by anaerobic digestion. The anaerobic digester 110 receives organic waste, such as livestock manure, food waste, or sewage, and performs anaerobic digestion. The anaerobic digester 110 decomposes organic waste into digestate and biogas using anaerobic microorganisms under an anaerobic condition in which oxygen does not exist. The biogas contains methane ($CH_4$) of about 60-70%, carbon dioxide ($CO_2$) of about 30-40%, and trace amounts of other substances, such as hydrogen sulfide.

The digestate generated by the anaerobic digestion in the anaerobic digester 110 is delivered to the solid-liquid separation tank 120, and the biogas is delivered to the gas-liquid dissolver 140.

The solid-liquid separation tank 120 receives the digestate of the organic waste decomposed by the anaerobic digester 110 and separates it into solid components and liquid components. The solid-liquid separation tank 120 separates the digestate into solid components and liquid components using various methods, such as by a filter press and a centrifugal dehydrator.

The solid-liquid separation tank 120 separates the solid components and the liquid components, and delivers the liquid components to the aerobic bioreactor (ammonia degassing tank, 130) and some of the solid components to the phosphorus recovery tank (ion reactor, 170) and the rest of the solid components to a sludge treatment facility (not shown). The solid-liquid separation tank 120 transfers all of the liquid components to the aerobic bioreactor (ammonia degassing tank, 130) to treat the ammonium ions contained in the liquid components. Meanwhile, the solid-liquid separation tank 120 delivers most (about 90%) of the solid components to an external sludge treatment facility (not shown). To extract phosphorus contained in the solid component, the conventional technique needs to use a large amount of chemicals (strong acids). To prevent this problem, the solid-liquid separation tank 120 delivers most of the separated solid components to an external sludge treatment facility (not shown). Meanwhile, the solid-liquid separation tank 120 delivers only some (about 10-50%) of the separated solid components to the phosphorus recovery tank (ion reactor, 170). The solid components transferred to the phosphorus recovery tank (ion reactor, 170) allow solid compounds to aggregate based on the solid components when an ion reaction occurs to generate the solid compounds in the phosphorus recovery tank (ion reactor, 170), thus increasing the efficiency of generating the compounds.

The aerobic bioreactor (ammonia degassing tank, 130) oxidizes the soluble organic matter in the liquid components separated in the solid-liquid separation tank 120 while degassing some of the ammonium ions into ammonia gas. Ammonium ions change their properties depending on changes in temperature and pH as illustrated in the graph of FIG. 5.

Figure 5:
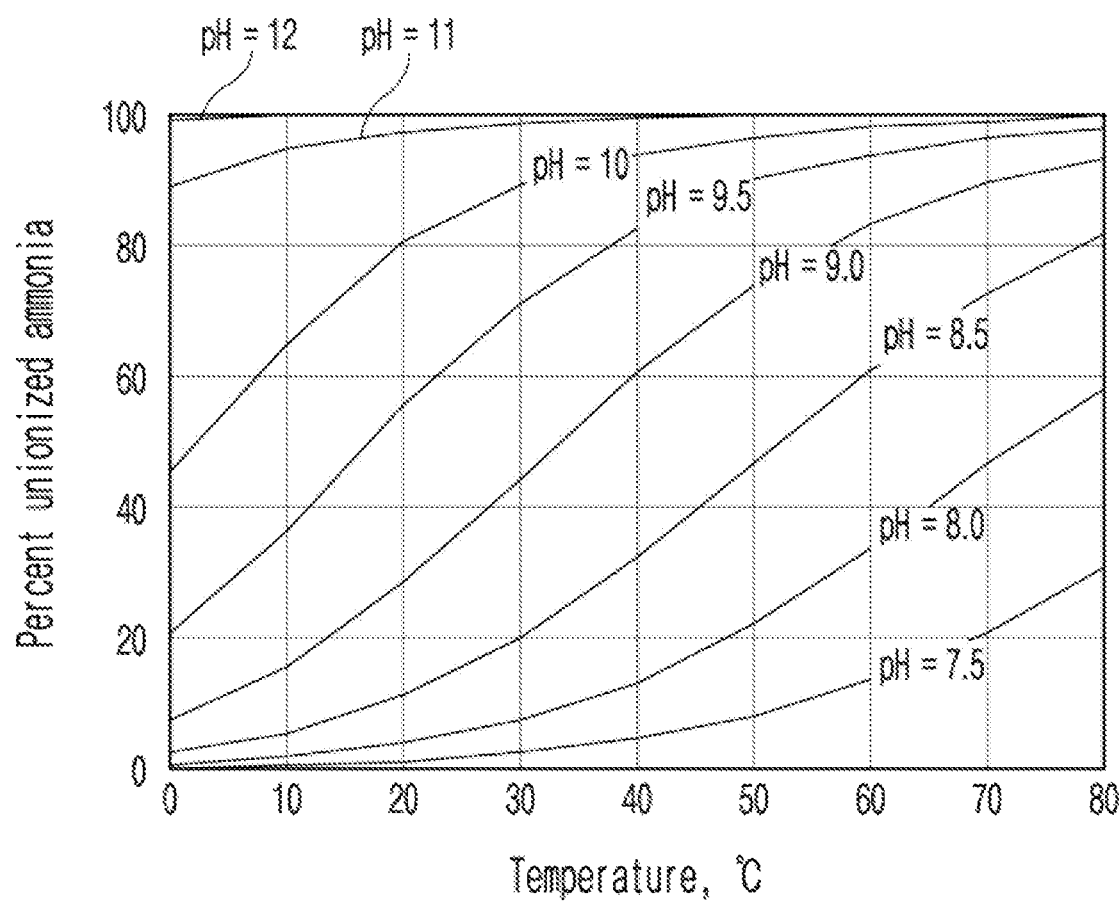
FIG. 5 is a graph illustrating a change in ammonia properties depending on the pH and temperature of ammonia.

FIG. 5 is a graph illustrating a change in ammonia properties depending on the pH and temperature of ammonia.

It may be identified that the degassing rate increases as the pH and the temperature increase. In other words, as the pH of the liquid containing ammonium ions increases or as the temperature of the liquid increases, more ammonium ions are degassed into ammonia gas.

Referring back to FIG. 1, a predetermined amount of air is injected (aerated) into the aerobic bioreactor (ammonia degassing tank, 130). The injected air raises the pH of the liquid components in the aerobic bioreactor (ammonia degassing tank, 130). As the pH of the liquid components increases, the degassing of ammonium ions contained in the liquid component into ammonia gas becomes active. Typically, the liquid components maintain the same state as that of the anaerobic digester 110, and may have a temperature of about 35° C. and a pH of about 7.5. In this state, when air is injected and the pH rises up to 9, 48.4% of ammonium ions may be degassed into ammonia gas. The amount of ammonia gas generated may be controlled by the amount of air to be injected, and the ammonia gas degassed in the aerobic bioreactor (ammonia degassing tank, 130) is injected into the gas-liquid dissolver 140.

The gas-liquid dissolver 140 mixes the biogas generated in the anaerobic digester and the ammonia gas degassed in the aerobic bioreactor (ammonia degassing tank, 130) with dissolution water and separates and discharges a specific gas using the difference in solubility in the dissolution water.

The gas-liquid dissolver 140 contains dissolution water (e.g., water) therein, receives the biogas generated in the anaerobic digestion tank and the ammonia gas degassed in the aerobic bioreactor (ammonia degassing tank, 130), and mixes a corresponding gas with the dissolution water. As described above, the biogas mainly contains methane and carbon dioxide. As the biogas is injected into the gas-liquid dissolver 140, only components having relatively high solubility in the dissolution water are dissolved in the dissolution water. The solubility in dissolution water is illustrated in FIG. 6.

Figure 6:
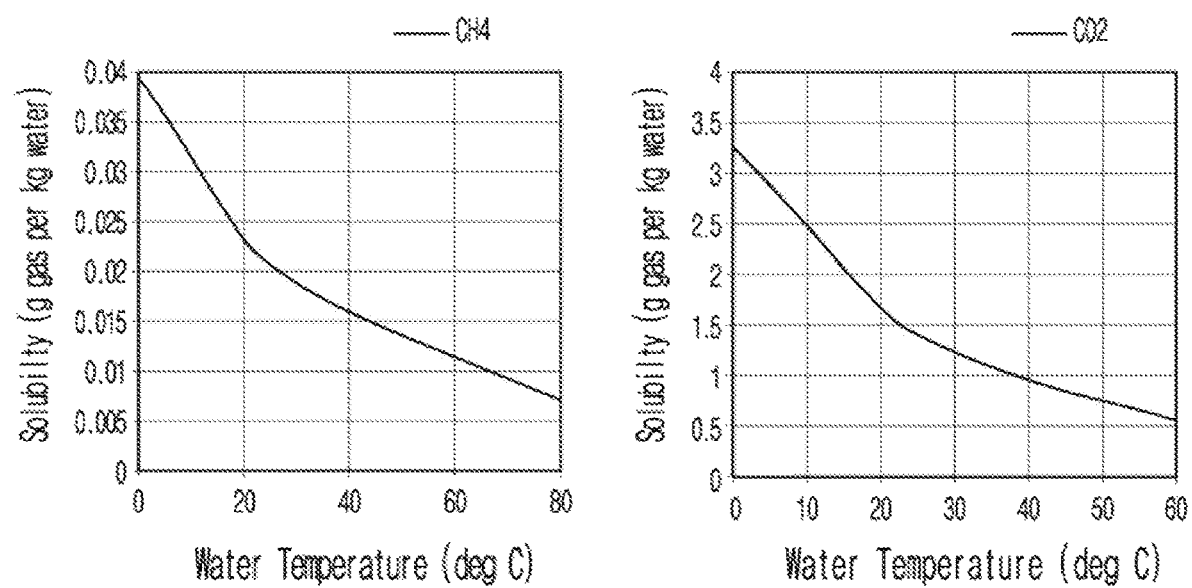
FIG. 6 is a graph illustrating the solubility of methane and carbon dioxide in water.

FIG. 6 is a graph illustrating the solubility of methane and carbon dioxide in water.

FIG. 6 illustrates the solubility of methane and carbon dioxide when the dissolution water is water. As may be seen in FIG. 6, the solubility of carbon dioxide is about 85 times higher than that of methane at the same temperature. In other words, when the biogas whose main components are methane and carbon dioxide is injected into the gas-liquid dissolver 140, most of the carbon dioxide is dissolved in the dissolution water, but most of the methane is not dissolved in the dissolution water while remaining in the gas state.

Referring back to FIG. 1, the gas-liquid dissolver 140 separates methane in the biogas using the difference in the solubility of the gas in the dissolution water. The gas-liquid dissolver 140 has the advantage of being able to separate a specific gas (methane) from the biogas by simply mixing the injected biogas with the dissolution water without a separate chemical or process. The gas-liquid dissolver 140 separates methane and discharges it to the gas storage tank 150.

Unlike methane, most of the carbon dioxide is dissolved in the dissolution water. Carbon dioxide is dissolved into hydrogen ions ($H^+$) and bicarbonate ions ($HCO_3^-$), and thus the pH of the dissolution water is lowered. The drop in the pH of the dissolution water changes the ammonia gas injected into the gas-liquid dissolver back into ammonium ions. Carbon dioxide is dissolved into hydrogen ions and bicarbonate ions and, when the pH of the dissolution water gradually decreases, the bicarbonate ions are dissolved into carbonate ions ($CO_3^{2-}$) and hydrogen ions. However, as ammonia gas together with carbon dioxide is injected into the gas-liquid dissolver 140, the hydrogen ions dissolved from the carbon dioxide and ammonia gas react, generating ammonium ions. Accordingly, the pH of the dissolution water is not lowered enough in such an extent as to dissolve the bicarbonate ions again, and ammonium ions and bicarbonate ions exist in the gas-liquid dissolver 140. As such, the gas-liquid dissolver 140 has an advantage of being able to create an environment for changing ammonia gas into ammonium ions without injecting a separate solution, by dissolving carbon dioxide having high solubility in ammonia gas and dissolution water.

The gas-liquid dissolver 140 delivers the ionized ammonium ions and bicarbonate ions to the compound production unit 160.

Waste gas including carbon dioxide may be introduced from the outside into the gas-liquid dissolver 140 in addition to the biogas generated in the anaerobic digester and the ammonia gas degassed in the aerobic bioreactor (ammonia degassing tank 130). Waste gas including carbon dioxide discharged from, e.g., a power plant, may be introduced into the gas-liquid dissolver 140, so that additional carbon dioxide may be dissolved into the dissolution water in the gas-liquid dissolver 140. The gas-liquid dissolver 140 may adjust the amount of dissolved carbon dioxide using the waste gas (including carbon dioxide) which is additionally introduced.

The gas storage tank 150 collects and stores the gas discharged from the gas-liquid dissolver 140.

As described above, the gas having a low solubility in the dissolution water, that is, methane gas, is discharged from the gas-liquid dissolver 140. The gas storage tank 150 collects and stores the gas discharged from the gas-liquid dissolver 140. Since methane gas is collected and stored in the gas storage tank 150, the effective resource recovery device 100 may conveniently collect and store methane gas generated in the organic waste treatment process.

The compound production unit 160 provides a preset environment to produce a solid compound with the ions dissolved in the dissolution water.

As described above, bicarbonate ions and ammonium ions are present in the dissolution water. The compound production unit 160 maintains the temperature below 30° C. and the pH above neutral, allowing the ions to bind together. The bicarbonate ions and the ammonium ions react at a mole ratio of 1:1 and, as a result, are combined into a solid compound in the form of ammonium bicarbonate. Since ammonium bicarbonate has a property of dissociation when the temperature is 36° C. or higher or when the pH is low, the compound production unit 160 provides the above-described environment so that the compound may be associated and produced. From the so-produced compound (ammonium bicarbonate), nitrogen is extracted.

The phosphorus recovery tank (ion reactor, 170) receives the liquid components which have passed through the aerobic bioreactor (ammonia degassing tank, 130), some of the solid components separated from the solid-liquid separation tank 120, and an ion-binding material and causes an ionic reaction, producing a solid phosphate compound.

The liquid components that have passed through the aerobic bioreactor (ammonia degassing tank, 130) contains various ions, such as some ammonium ions, phosphorus in the form of phosphate ions, and other hydroxide ions. Further, the phosphorus recovery tank (ion reactor, 170) receives an ion-binding material that is to cause an ionic reaction with the above-described liquid components from the outside. Here, the ion-binding material is a material that is combined with the phosphate ions and other ions contained in the liquid components to cause an ionic reaction, thereby producing a solid (sediment form) phosphate compound, and may include, e.g., magnesium oxide (MgO) or calcium oxide (CaO). The liquid components and ion-binding material that have passed through the aerobic bioreactor (ammonia degassing tank, 130) cause an ionic reaction in the phosphorus recovery tank (ion reactor, 170) and are produced as a solid phosphate compound. Assuming that the ion-binding material is magnesium oxide, the ammonium ions, phosphate ions, and magnesium ions react in a mole ratio of 1:1:1 in the phosphorus recovery tank (ion reaction tank, 170), so that a solid phosphate compound, e.g., struvite, is formed. Assuming that the ion-binding material is calcium oxide, the calcium ions, phosphate ions, and hydroxide ions react in a mole ratio of 5:3:1, forming a sold phosphate compound, e.g., hydroxyapatite. Magnesium oxide (MgO) or calcium oxide (CaO) is mentioned as an example of the ion-binding material but, without limitations thereto, may be replaced with any other material that may be combined with the phosphorus in the liquid components to thereby form a solid phosphate compound.

If the ammonium ions in the phosphorus recovery tank (ion reactor, 170) are used for the production of the solid phosphate compound, the amount of ammonium ions may be adjusted by the amount of ammonia gas degassed in the aerobic bioreactor (ammonia degassing tank, 130). As described above, if struvite is produced as the solid phosphate compound, the ammonium ions are combined with the phosphate ions in a mole ratio of 1:1, and the amount of ammonium ions may be insufficient or large. In this case, the amount of ammonium ions remaining after passing through the aerobic bioreactor (ammonia degassing tank, 130) may be adjusted by adjusting the amount of air injected into the aerobic bioreactor (ammonia degassing tank, 130).

Further, some of the solid components that have not been transferred to the sludge treatment facility (not shown) among the solid components separated in the solid-liquid separation tank 120 are delivered to the phosphorus recovery tank (ion reactor, 170). The solid components delivered to the phosphorus recovery tank (ion reactor, 170) serves as a seed, thereby increasing the efficiency of production of the solid phosphate compound. Since the solid phosphate compound is produced based mainly on the delivered solid components, the solid phosphate compound is more efficiently produced. The so-produced solid phosphate compound is delivered to the recovery unit 180.

Phosphorus may be extracted from the solid phosphate compound produced by an ionic reaction in the phosphorus recovery tank (ion reactor, 170).

The recovery unit 180 recovers the solid compound delivered from the compound production unit 160 and the solid phosphate compound delivered from the phosphorus recovery tank (ion reactor, 170). The recovery unit 180 may recover nitrogen and phosphorus by recovering the solid compound (ammonium bicarbonate) and the solid phosphate compound. As such, the nitrogen and phosphorus components recovered from the organic waste by the effective resource recovery device may be recycled in various products, e.g., fertilizers.

Figure 2:
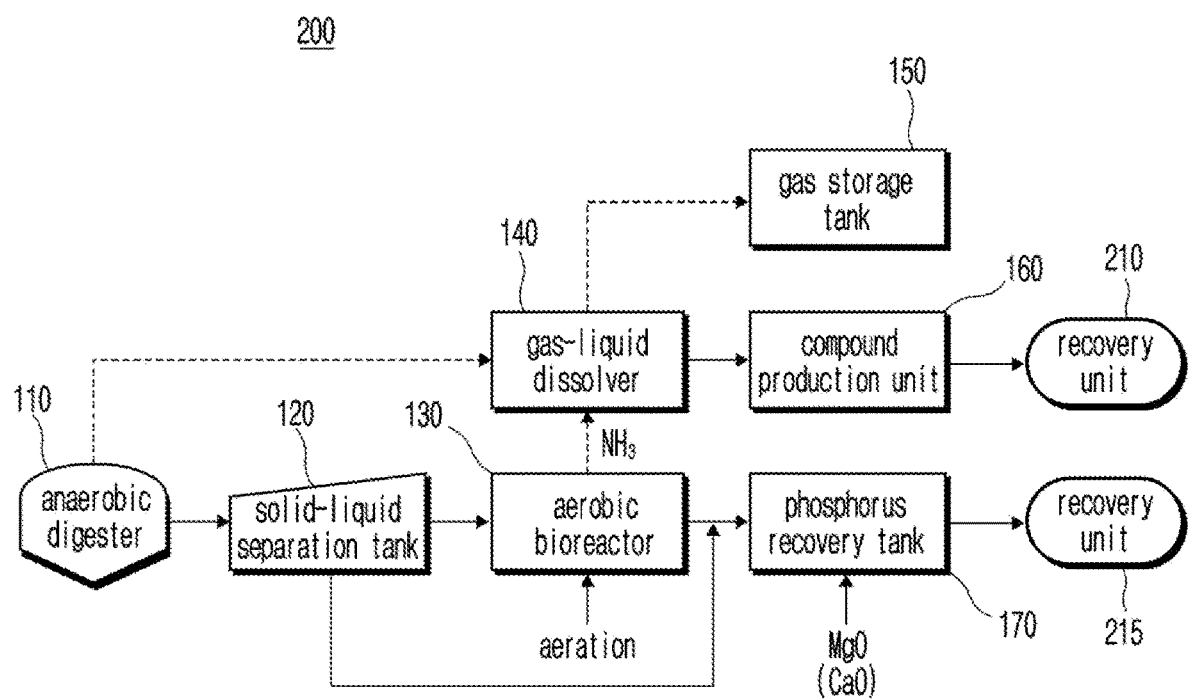
FIG. 2 is a view illustrating a configuration of an effective resource recovery device according to a second embodiment of the present invention.

FIG. 2 is a view illustrating a configuration of an effective resource recovery device according to a second embodiment of the present invention.

Referring to FIG. 2, an effective resource recovery device 200 according to a second embodiment of the present invention includes a plurality of recovery units 210 and 215 in the configuration of the effective resource recovery device 100.

The recovery units 210 and 215 are connected to the compound production unit 160 and the phosphorus recovery tank (ion reactor, 170), respectively, to recover the compound (ammonium bicarbonate) produced in the compound production unit 160 and the phosphate compound produced in the phosphorus recovery tank (ion reactor, 170). The nitrogen component included in the compound and the phosphorus component included in the phosphorus compound may be mixed and used together or separately in, e.g., fertilizers. When the nitrogen component and the phosphorus component need to be used separately, recovering them by one recovery unit may cause the inconvenience of the need for separating the compound and the phosphorus compound. To address this inconvenience, the effective resource recovery device 200 connects the recovery units 210 and 215 to the compound production unit 160 and the phosphorus recovery tank (ion reactor, 170), respectively, to recover the nitrogen component and the phosphorus component, respectively.

Figure 3:
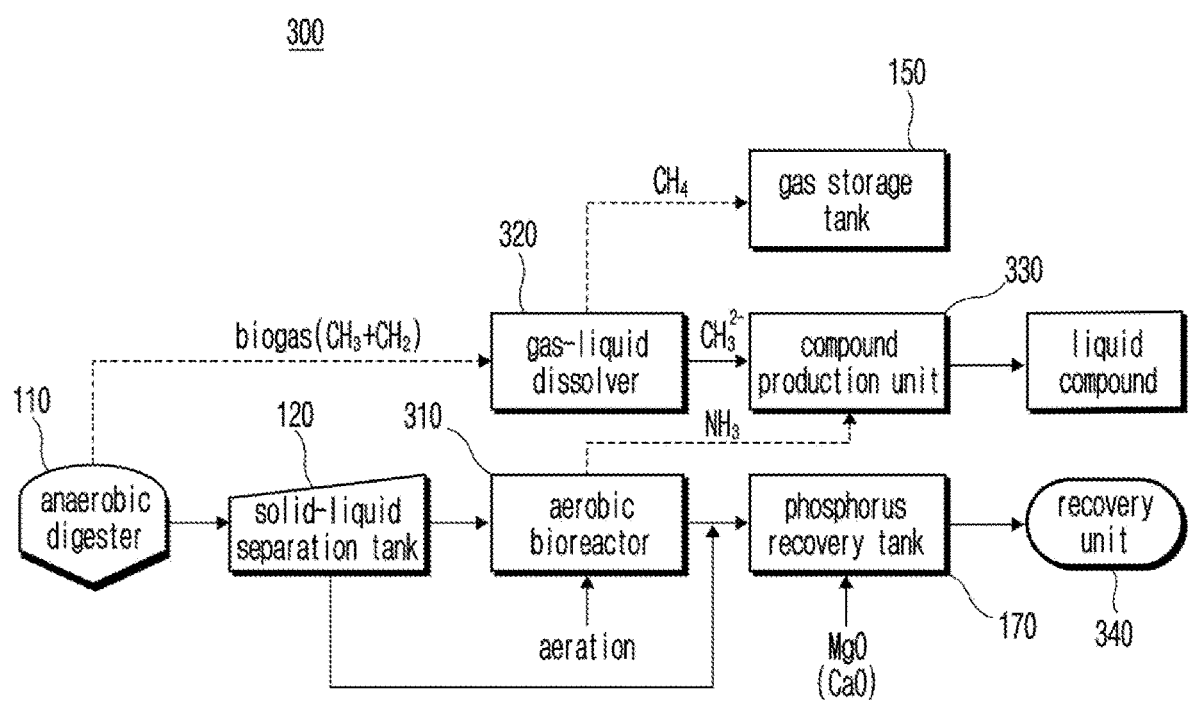
FIG. 3 is a view illustrating a configuration of an effective resource recovery device according to a third embodiment of the present invention.

FIG. 3 is a view illustrating a configuration of an effective resource recovery device according to a third embodiment of the present invention.

Referring to FIG. 3, an effective resource recovery device 300 according to a third embodiment of the present invention includes an ammonia degassing tank 310, a gas-liquid dissolver 320, a compound production unit 330, and a recovery unit 340 that play different roles from those of the effective resource recovery device 100.

The ammonia degassing tank 310 degasses some of the ammonium ions in the liquid components separated by the solid-liquid separation tank 120 into ammonia gas. Whereas the aerobic bioreactor (ammonia deaeration tank, 130) injects ammonia gas into the gas-liquid dissolver 120, the ammonia degassing tank 310 directly injects the degassed ammonia gas into the compound production unit 330.

The gas-liquid dissolver 320 mixes only the biogas generated in the anaerobic digester 110 with the dissolution water. As described above, due to the difference in the solubility, in the dissolution water, of methane and carbon dioxide in the biogas, a high concentration of methane is separated and discharged into the gas storage tank 150, and only carbon dioxide is dissolved in the dissolution water. Carbon dioxide dissolved in the dissolution water is first dissolved into hydrogen ions and bicarbonate ions in the gas-liquid dissolver 320 and is additionally dissolved into hydrogen ions and carbonate ions.

Since ammonia, together with the biogas, is injected into the gas-liquid dissolver 140 illustrated in FIG. 1, if carbon dioxide is first dissolved, hydrogen ions and ammonia gas react to produce ammonium ions. For this reason, a pH sufficient to further dissolve bicarbonate ions into hydrogen ions and carbonate ions is not formed in the gas-liquid dissolver 140, so that carbon dioxide is dissolved up into the bicarbonate ions in the gas-liquid dissolver 140.

However, since only biogas is injected into the gas-liquid dissolver 320 but no ammonia gas is injected, only carbon dioxide is wholly dissolved in the dissolution water. First, carbon dioxide is dissolved into hydrogen ions and bicarbonate ions. As described above, since ammonia gas is not injected, the pH of the dissolution water gradually decreases as carbon dioxide is dissolved. Accordingly, bicarbonate ions are additionally dissolved into hydrogen ions and carbonate ions. Biogas (carbon dioxide) exists in the gas-liquid dissolver 320 until it is completely dissolved in the dissolution water, and accordingly, is finally dissolved into carbonate ions and hydrogen ions.

The gas-liquid dissolver 320 delivers the carbonate ions and hydrogen ions to the compound production unit 330.

The compound production unit 330 provides a preset environment to produce a liquid compound from the ions dissolved in dissolution water and the ammonia gas from the ammonia degassing tank 310.

The ammonia gas is made into ammonium ions by the hydrogen ions dissolved in the dissolution water injected into the compound production unit 330. However, since carbon dioxide is dissolved up into carbonate ions, but not into bicarbonate ions, in the gas-liquid dissolver 320, the carbonate ions and ammonium ions separately remain in the ionic state in the compound production unit 330, thereby producing a liquid compound. The so-produced liquid compound may be used in various applications using ammonium ions, e.g., fertilizer (liquid fertilizer).

Meanwhile, the recovery unit 340 recovers only the solid phosphate compounds produced in the phosphorus recovery tank (ion reactor, 170). As described above, since the compound production unit 330 produces a liquid compound, the recovery unit 340 recovers only the solid phosphate compound from the phosphorus recovery tank (ion reactor, 170).

Figure 4:
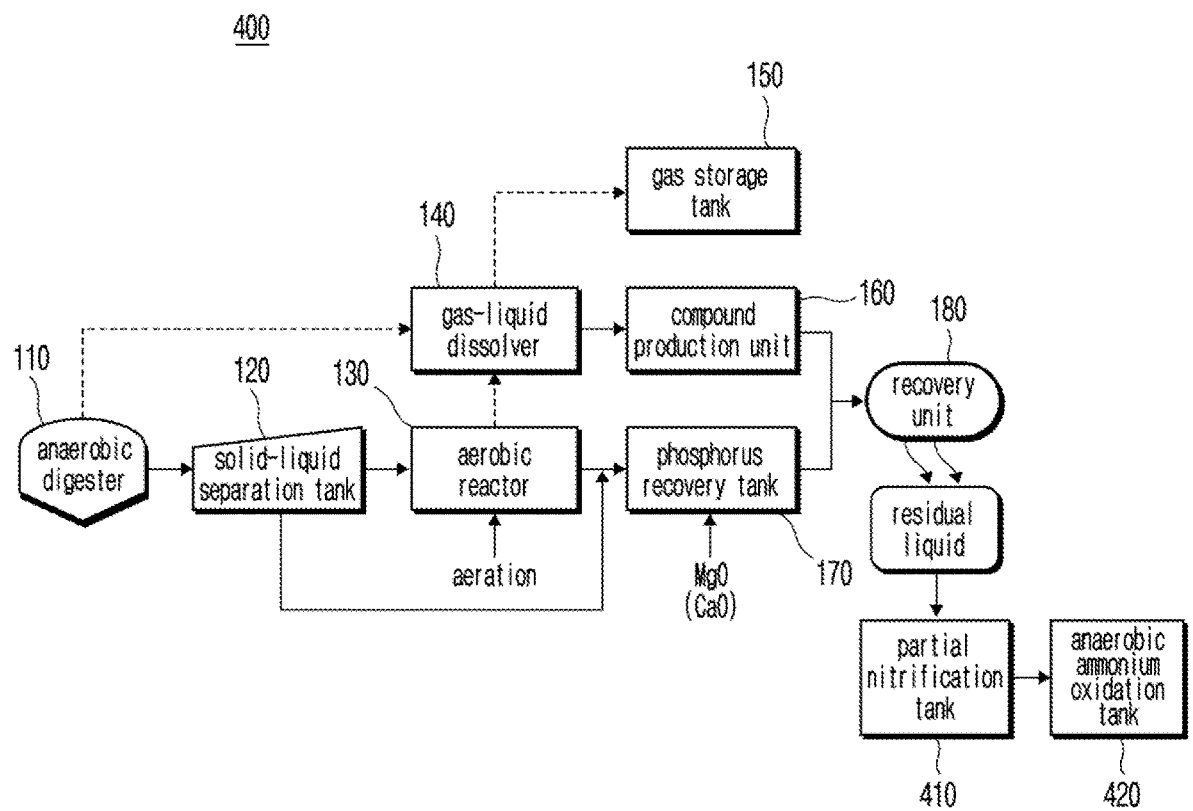
FIG. 4 is a view illustrating a configuration of an effective resource recovery device according to a fourth embodiment of the present invention.

FIG. 4 is a view illustrating a configuration of an effective resource recovery device according to a fourth embodiment of the present invention.

Referring to FIG. 4, an effective resource recovery device 400 according to a fourth embodiment of the present invention includes a partial nitrification tank 410 and an anaerobic ammonium oxidation tank 420 in addition to the configuration of the effective resource recovery device 100.

The nitrogen component (ammonia gas or ammonium ions) in the liquid component separated in the solid-liquid separation tank 120 is degassed into ammonia gas to form a solid compound, or is used for the production of phosphate compounds in the phosphorus recovery tank (ion reactor, 170) and is thus mostly removed. However, despite passing through each component, there may be a nitrogen component that does not react and remains in the liquid components. The liquid components are discharged in the filtrate when the compound or phosphate compound is recovered by the recovery unit 180, and nitrogen components may remain in the liquid component discharged in the filtrate.

The partial nitrification tank 410 converts some of the ammonium ions present in the liquid components into nitrite ions. The partial nitrification tank 410 includes ammonium oxidizing bacteria and nitrite oxidizing bacteria and converts some of ammonium ions into nitrite ions or converts nitrite ions into nitrate ions.

The anaerobic ammonium oxidation tank 420 converts ammonium ions and nitrite ions into nitrogen gas, thereby removing the nitrogen components in the liquid component. The anaerobic ammonium oxidation tank 420 includes bacterial growing in an anaerobic environment and converts ammonium ions and nitrite ions into nitrogen gas, thereby removing the nitrogen components remaining in the liquid components.

Figure 7:
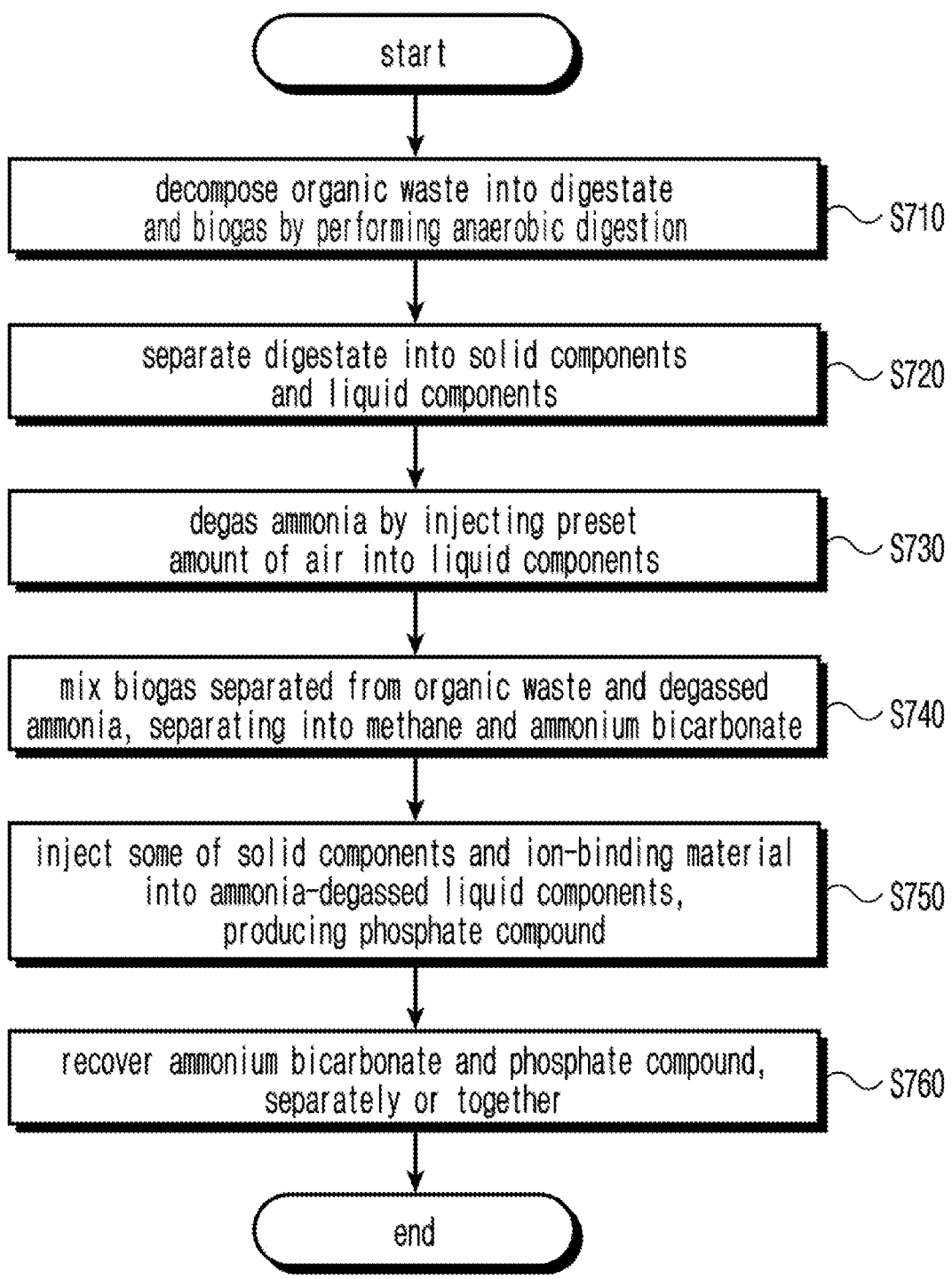
FIG. 7 is a flowchart illustrating an effective resource recovery method according to a first embodiment of the present invention.

FIG. 7 is a flowchart illustrating an effective resource recovery method according to the first embodiment of the present invention.

The anaerobic digester 110 decomposes organic waste into digestate and biogas by anaerobic digestion (S710). The biogas is delivered to the gas-liquid dissolver 140, and the digestate is delivered to the solid-liquid separation tank 120.

The solid-liquid separation tank 120 separates the digestate into solid components and liquid components (S720). The solid-liquid separation tank 120 separates the solid components and the liquid components, transfers most of the solid components to a sludge treatment facility (not shown) while transferring only some to the phosphorus recovery tank (ion reactor, 170), and transfers the liquid components to the aerobic bioreactor (ammonia degassing tank, 130).

The aerobic bioreactor (ammonia degassing tank, 130) degasses ammonia by injecting a predetermined amount of air into the liquid components (S730). As air is injected into the aerobic bioreactor (ammonia degassing tank, 130) to increase the pH, some of the ammonium ions contained in the liquid component are degassed into ammonia gas.

The gas-liquid dissolver 140 and the compound production unit 160 mix the biogas separated from organic waste and the degassed ammonia, separating them into methane and ammonium bicarbonate (S740). The biogas and ammonia introduced into the gas-liquid dissolver are mixed with the dissolution water contained in the gas-liquid dissolver 140, and are separated by a difference in solubility in the dissolution water. Methane gas having low solubility in the dissolution water is not dissolved in the dissolution water and remains in a gaseous state, and is discharged to the gas storage tank 150. On the other hand, carbon dioxide having high solubility in dissolution water is dissolved into hydrogen ions and bicarbonate ions in the dissolution water and is mixed with the dissolution water whose pH is lowered by carbon dioxide, and ammonia gas is also changed to ammonium ions. In the environment of the compound production unit 160, bicarbonate ions and ammonium ions are combined, producing ammonium bicarbonate which is a solid compound.

The phosphorus recovery tank (ion reactor, 170) produces a phosphate compound by injecting some of the solid components and an ion-binding material into the ammonia-degassed liquid components (S750). The ion-binding material and ions, including phosphate ions, contained in the liquid components cause an ionic reaction, producing a solid phosphate compound. Here, the ion-binding material is a material that causes an ionic reaction with the phosphate ions contained in the liquid components to produce a sold phosphate compound. In this case, when some of the solid components separated in the solid-liquid separation tank 120 are added together, a solid phosphate compound is produced more efficiently.

The recovery unit 180 recovers the ammonium bicarbonate and the phosphate compound, separately or together (S760).

Figure 8:
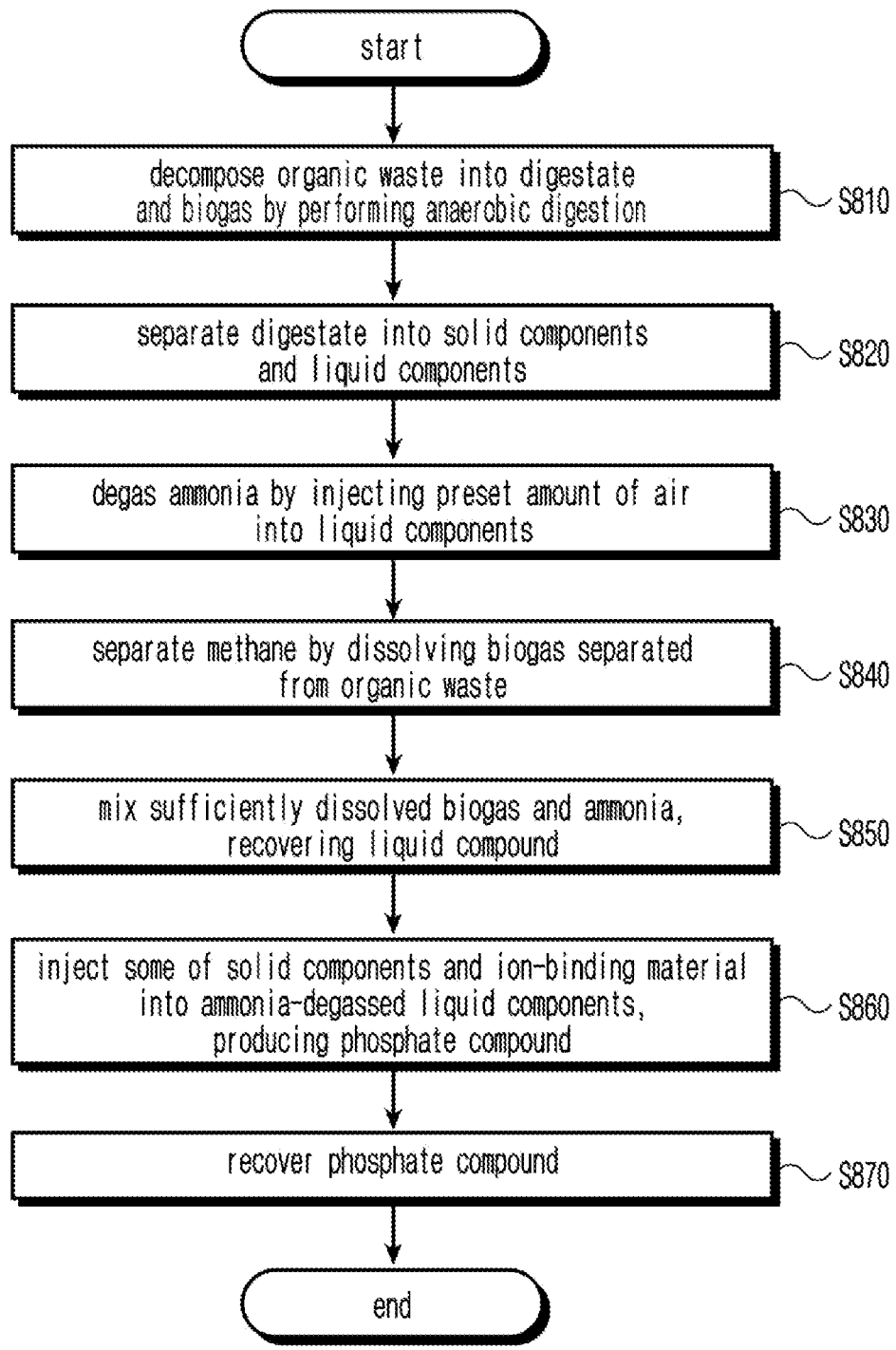
FIG. 8 is a flowchart illustrating an effective resource recovery method according to a second embodiment of the present invention.

FIG. 8 is a flowchart illustrating an effective resource recovery method according to the second embodiment of the present invention.

The anaerobic digester 110 decomposes organic waste into digestate and biogas by anaerobic digestion (S810).

The solid-liquid separation tank 120 separates the digestate into solid components and liquid components (S820).

The ammonia degassing tank 310 degasses ammonia by injecting a predetermined amount of air into the liquid components (S830).

The gas-liquid dissolver 320 separates methane by dissolving the biogas separated from the organic waste (S840).

The compound production unit 330 recovers the liquid compound by mixing sufficiently dissolved biogas and ammonia (S850). The ammonia gas degassed in step S830 and the carbon dioxide dissolved in step S840 are injected into the compound production unit 330. The compound production unit 330 recovers the liquid compound by mixing ammonia gas and sufficiently dissolved carbon dioxide.

The phosphorus recovery tank (ion reactor, 170) produces a phosphate compound by injecting some of the solid components and an ion-binding material into the ammonia-degassed liquid components (S860).

The recovery tank 340 recovers the phosphate compound (S870).

Figure 9:
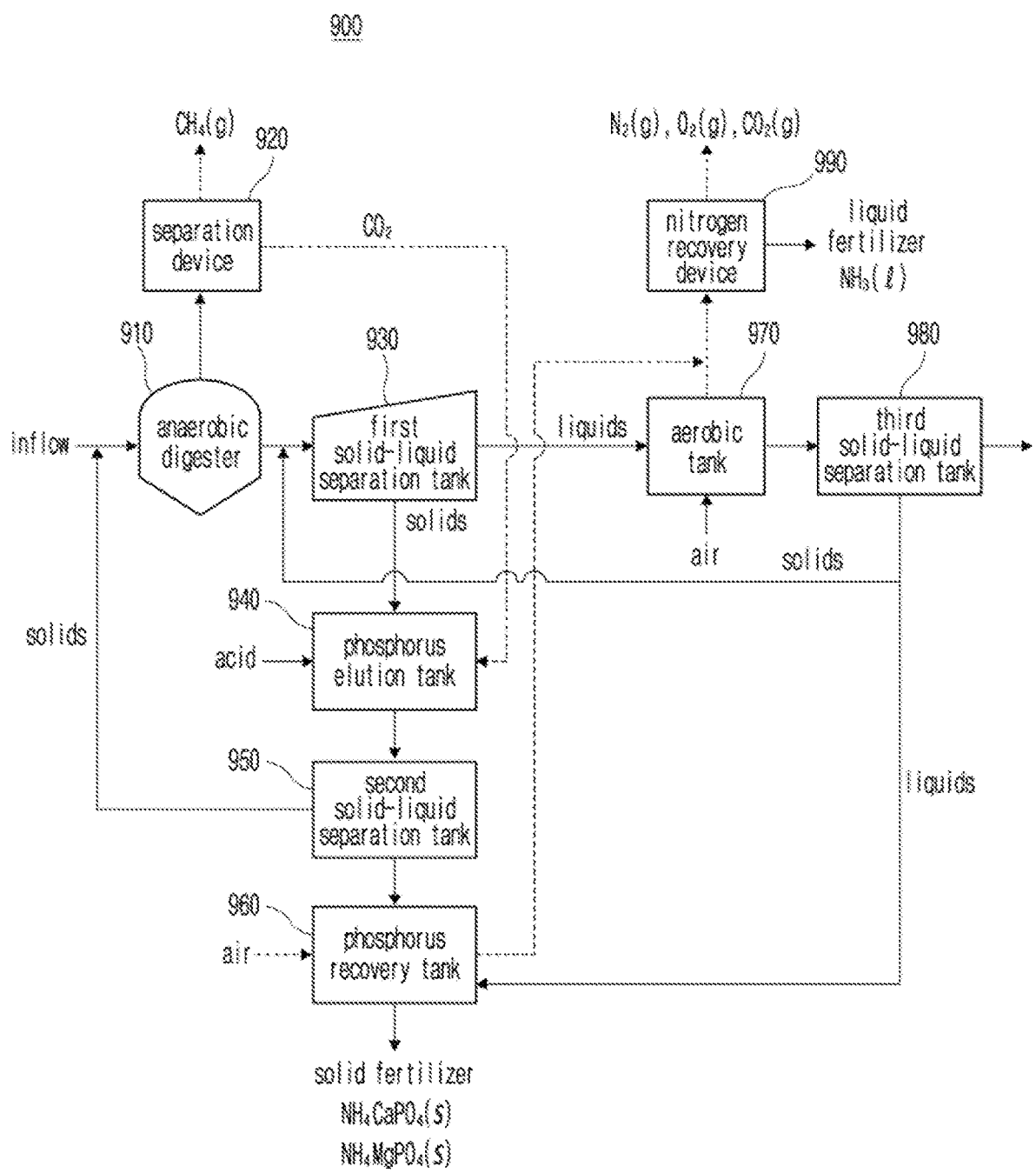
FIG. 9 is a view illustrating a configuration of an effective resource recovery device according to an embodiment of the present invention.

FIG. 9 is a view illustrating a configuration of an effective resource recovery device according to an embodiment of the present invention.

Referring to FIG. 9, an effective resource recovery device 900 according to an embodiment of the present invention includes an anaerobic digester 910, a separation device 920, a first solid-liquid separation tank 930, a phosphorus elution tank 940, a second solid-liquid separation tank 950, a phosphorus recovery tank 960, an aerobic tank 970, a third solid-liquid separation tank 980, and a nitrogen recovery device 990.

The anaerobic digester 910 decomposes organic waste into digestate and biogas by anaerobic digestion. The anaerobic digester 910 receives organic waste, such as livestock manure, food waste, or sewage, and performs anaerobic digestion. The anaerobic digester 910 decomposes organic waste into digestate and biogas using anaerobic microorganisms under an anaerobic condition in which oxygen does not exist. The biogas contains methane ($CH_4$) of about 60-70%, carbon dioxide ($CO_2$) of about 30-40%, and trace amounts of other substances, such as hydrogen sulfide ($H_2S$) and siloxane ($R_2SiO$).

The digestate generated by the anaerobic digestion in the anaerobic digester 910 is delivered to the solid-liquid separation tank 920, and the biogas is delivered to the separation device 920.

Before the organic waste is introduced into the anaerobic digester 910, a pretreatment process may be performed on the organic waste. The pretreatment process is performed so as not to cause a problem in the operation of the anaerobic digester 910 after the organic waste is introduced into the anaerobic digester 910. For example, the pretreatment process may include a process for removing foreign substance, which may damage the anaerobic digestion tank 910, in the organic waste.

The separation device 920 receives the biogas generated in the anaerobic digester 910, separates and discharges each component included in the biogas. As described above, the biogas is mostly composed of methane and carbon dioxide. The separation device 920 receives the biogas and separates and discharges methane and carbon dioxide. Furthermore, the separation device 920 may additionally separate trace amounts of components included in the biogas.

One method for separating methane and carbon dioxide by the separation device 920 is to use the difference in solubility between both the gases. The separation device 920 includes dissolution water (e.g., water) therein, and receives the biogas generated in the anaerobic digester 910 and mixes the dissolution water and the gas. In this case, when the dissolution water is water, the solubility of carbon dioxide is about 85 times higher than that of methane at the same temperature. In other words, when the biogas whose main components are methane and carbon dioxide is injected into the separation device 920, most of the carbon dioxide is dissolved in the dissolution water, but most of the methane is not dissolved in the dissolution water while remaining in the gas state.

The separation device 920 may separate methane in the biogas using the difference in the solubility of the gas in the dissolution water. The separation device 920 has the advantage of being able to separate a specific gas (methane) from the biogas by simply mixing the injected biogas with the dissolution water without a separate chemical or process. The separation device 920 separates methane in a gaseous state and separates carbon dioxide dissolved in dissolution water, in a gaseous state, through a separate degassing process. The separation device 920 delivers the separated carbon dioxide to the phosphorus elution tank 940.

The first solid-liquid separation tank 930 receives the digestate of the organic waste decomposed by the anaerobic digester 910 and separates it into solid components and liquid components. A large amount of solids and nitrogen/phosphorus are present in the digestate of organic waste. In general, nitrogen contained in livestock manure exists in a liquid phase, and phosphorus exists in a solid phase. As organic waste is liquefied while passing through the anaerobic digestion tank 910, dissolved nitrogen increases. Although phosphorus is also converted from solid phosphorus to dissolved phosphorus, the concentration of dissolved phosphorus does not significantly increase because phosphorus becomes solid by reaction with various cations present in the water during the conversion. The first solid-liquid separation tank 930 separates the solid components and the liquid components, and transfers the solid components to the phosphorus elution tank 940 and the liquid components to the aerobic tank 970. The first solid-liquid separation tank 930 may use various methods, such as using a filter press, a centrifugal dehydrator, a belt press, or dissolved air flotation.

The phosphorus elution tank 940 provides a preset environment to elute a preset component of the solid components separated in the first solid-liquid separation tank 930.

The phosphorus elution tank 940 elutes phosphorus among the solid components separated in the first solid-liquid separation tank 930. To effectively elute the solid phosphorus, a low pH environment (usually a pH of 2-3) needs to be provided. In this case, a significant amount of chemicals (acids) may be consumed to lower the pH from the pH of a neutral environment to the pH of 2 to 3. To address such an issue, the carbon dioxide separated in the separation device 920 is introduced into the phosphorus elution tank 940. In general, about 98% of high-concentration carbon dioxide is recovered from the separation device 920. This high concentration of carbon dioxide flows into the phosphorus elution tank 940, and the pH of the phosphorus elution tank 940 decreases to about 4.0. Accordingly, it may suffice to lower the pH in the phosphorus elution tank 940 from 4.0 to 2.0 to 3.0. Therefore, the amount of chemicals to be used for lowering the pH may be considerably reduced. This may be identified in the graph of FIG. 11.

Figure 11:
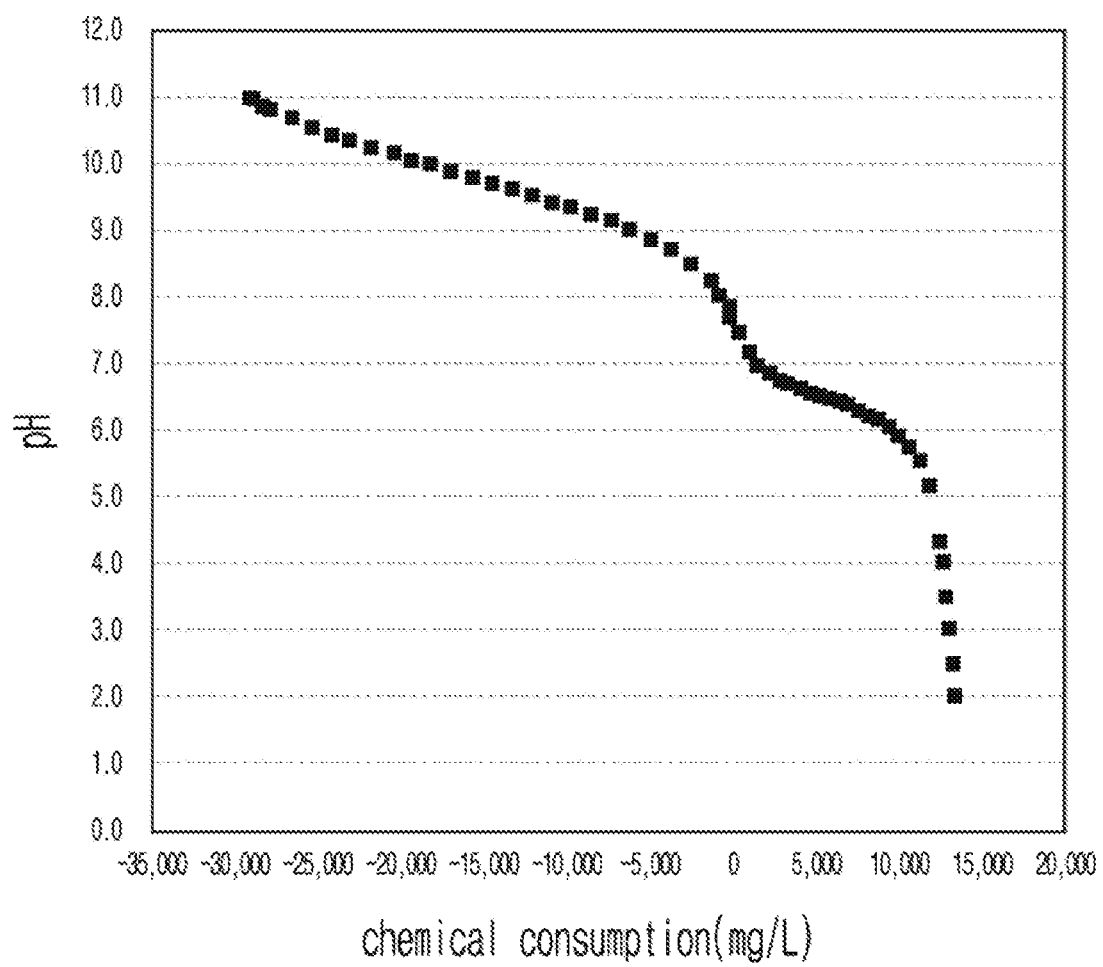
FIG. 11 is a graph illustrating the relationship between the pH and the amount of chemical consumption required to make each pH.

FIG. 11 is a graph illustrating the relationship between the pH and the amount of chemical consumption required to make each pH.

Referring to FIG. 11, it may be identified that the consumption of chemicals used to decrease the pH from 4.0 to 1.0 to 3.0 is not large, but a considerably large amount of chemicals need to consume when decreasing the pH from 7.0 to 4.0.

Referring back to FIG. 9, only the solid components primarily solid-liquid separated are introduced into the phosphorus elution tank 940, but the liquid components are not introduced into the phosphorus elution tank 940. Liquids with a fairly high alkalinity are present in the liquid components. Thus, if the liquid components are also included, more chemicals need be consumed to lower the pH. As only the solid components are introduced into the phosphorus elution tank 940, the amount of chemicals consumed to lower the pH is further reduced.

Furthermore, the concentration of solids in the digestate that flows out from the anaerobic digestion tank is around 5%, whereas the concentration of the solids flowing into the phosphorus elution tank 940 after solid-liquid separation is about 16.5% or more, which is about three times higher than that of digestate that does not undergo solid-liquid separation. Therefore, the volume of the phosphorus elution tank 940 in which the pH needs to drop to have the preset environment may be reduced by 30% or more, so that the consumption of chemicals to lower the pH is relatively reduced by about 30%. Thus, although the volume of the phosphorus elution tank 940 is reduced by about 30% as compared with the conventional one, the digestate may be sufficiently processed. In the phosphorus elution tank 940, since the phosphorus component is eluted from the high-concentration solid components, the concentration of the eluted phosphorus is about 5,000 mg/L to 6,000 mg/L, which is about 16.7 to 20 times higher than in a general case.

Due to the above-described characteristics, it is possible to reduce chemical consumption by up to 98.2% compared to the prior art in allowing the phosphorus elution tank 940 to have the preset environment.

The second solid-liquid separation tank 950 separates the components eluted via the phosphorus elution tank 940 and the remaining solids. Since most of the phosphorus components are eluted while passing through the phosphorus elution tank 940, the second solid-liquid separation tank 950 may separate the solids and liquid components by simple precipitation without any additional component. The precipitated solids are left with their cells destroyed by the acidic environment while passing through the phosphorus elution tank 940 and, thus, are transferred to the anaerobic digester 910 for use in methane production.

The recovery tank 960, which is a phosphorus recovery tank 960, receives the liquid components separated in the second solid-liquid separation tank 950 and deposits a predetermined component of the liquid components.

The phosphorus recovery tank 960 recovers phosphorus in the liquid components which have passed through the second solid-liquid separation tank 950. A fairly high-concentration of phosphorus component is contained in the liquid components eluted from the phosphorus elution tank 940 and passed through the second solid-liquid separation tank 950. Typically, unlike in elution, the pH needs to be maintained in a basic environment of pH 8.5 or higher to recover the eluted phosphorus component. However, according to the present invention, since a high concentration of phosphorus is contained in the liquid components introduced through the first solid-liquid separation tank 930 and the phosphorus elution tank 940 to the phosphorus recovery tank 960, more than 10% of phosphorus may be recovered even in a neutral environment with a pH of 7. Further, the phosphorus recovery tank 960 receives liquids from the third solid-liquid separation unit 980. Since the liquids separated in the third solid-liquid separation unit 980 have a pH raised while passing through the aerobic tank 970, the pH in the phosphorus recovery tank 960 may easily be maintained as the pH of the neutral environment by receiving the separated liquids from the third solid-liquid separation unit 980 without using separate chemicals. Further, air is injected into the phosphorus recovery tank 960, agitation necessary for phosphorus recovery is performed, and the dissolved carbon dioxide present in the liquid introduced into the phosphorus recovery tank 960 is degassed to raise the pH in the phosphorus recovery tank 960. While undergoing such process, the phosphorus recovery tank 960 recovers phosphorous in various forms, depending on the types and concentrations of the ions contained in the liquid components, such as $NH_4MgPO_4 \cdot 6H_2O$ or $NH_4CaPO_4 \cdot 6H_2O$. Further, as the phosphorus recovery tank 960 has a neutral pH environment, ammonia nitrogen eluted with phosphorus may be degassed due to an increase in pH. The degassed ammonia gas is delivered to the nitrogen recovery device 990.

The aerobic tank 970 provides an aerobic environment, receives the separated liquid components from the first solid-liquid separation tank 930, and removes organic matter.

By air injection, the aerobic tank 970 has an aerobic environment, and carbon dioxide in the liquid components introduced into the aerobic tank is degassed. Carbon dioxide is degassed, and the pH of the liquid components introduced into the aerobic tank rises. Accordingly, in the aerobic tank 970, degassing of liquid nitrogen (ammonium ions) proceeds. The reason why nitrogen degassing proceeds is described below with reference to FIG. 10.

Figure 10:
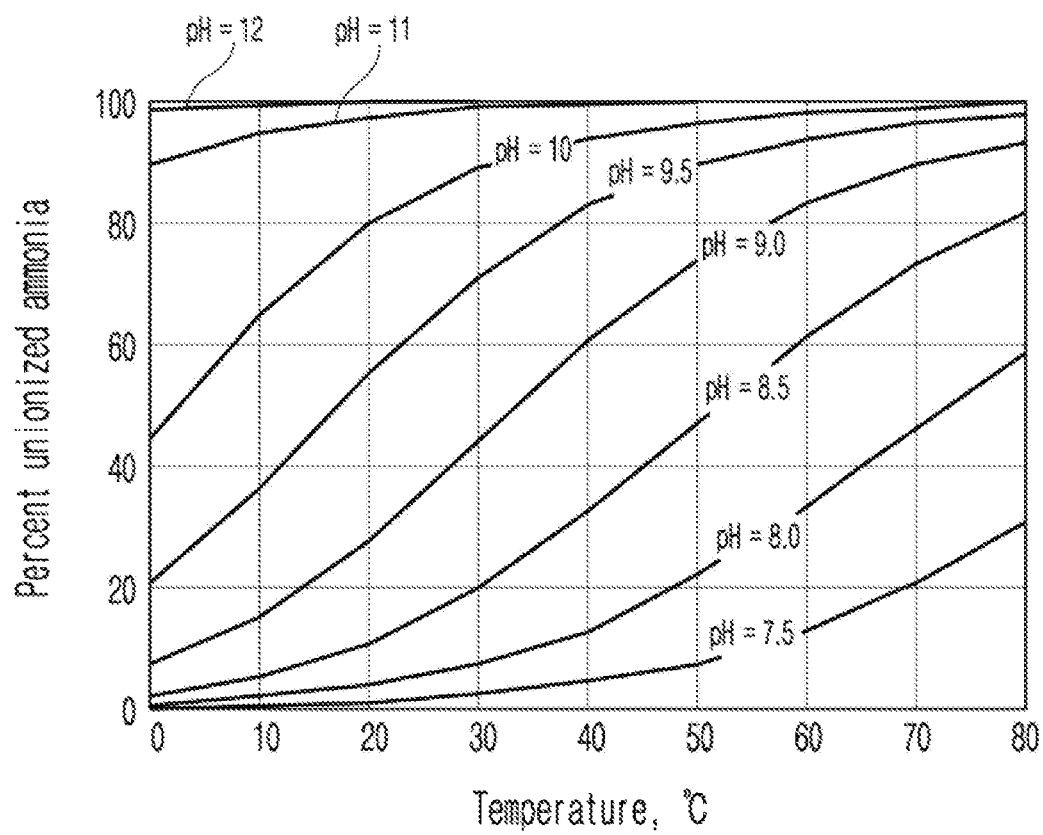
FIG. 10 is a graph illustrating a change in ammonia properties depending on the pH and temperature of ammonia.

FIG. 10 is a graph illustrating a change in ammonia properties depending on the pH and temperature of ammonia.

It may be identified that the degassing rate increases as the pH and the temperature increase. In other words, as the pH of the liquid containing ammonium ions increases or as the temperature of the liquid increases, more ammonium ions are degassed into ammonia gas.

Referring back to FIG. 9, the pH of the liquid components introduced into the aerobic tank 970 rises, and about 50% to 60% of the liquid nitrogen is degassed.

The pH of the liquid components introduced into the aerobic tank 970 rises, and the dissolved phosphorus remaining in the liquid components undergoes chemical bonding to form solids.

Figure 12:
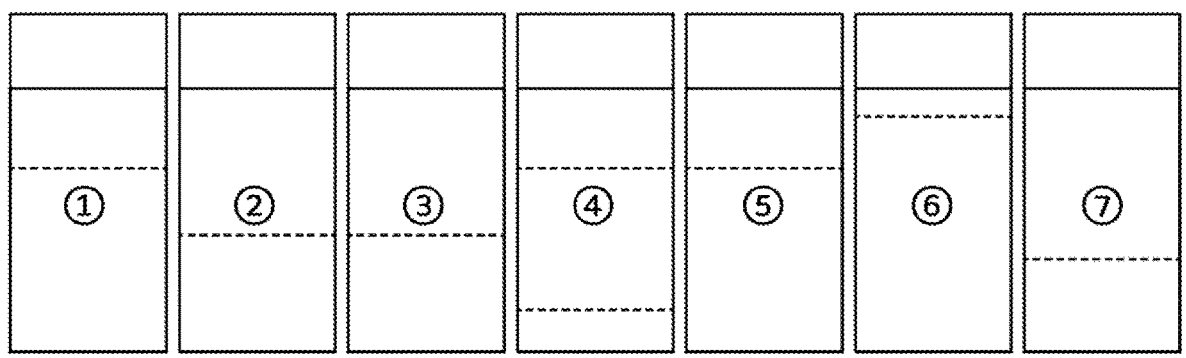
FIG. 12 is a view illustrating a difference in solids precipitation degree between organic waste that has passed through an effective resource recovery device and organic waste that has not passed through the effective resource recovery device according to an embodiment of the present invention.

The third solid-liquid separation tank 980 separates the liquid components and the solid components that have passed through the aerobic tank 970. After passing through the aerobic tank 970 having an aerobic environment, the dissolved phosphorus in the liquid components introduced into the aerobic tank 970 forms solids. As the dissolved phosphorus forms solids, the third solid-liquid separation tank 980 may separate the solid phosphorus from the liquid components without injecting a separate chemical for recovering phosphorus. The third solid-liquid separation tank 980 may separate the solids and liquids using a mechanical device, such as flotation separation. The introduced liquid components may be injected and retained in a storage facility, e.g., Pond, for, e.g., one to two months while separating the liquid components and the solid components. FIG. 12 illustrates the degree of separation of the liquid components and solid components depending on each circumstance.

FIG. 12 is a view illustrating a difference in solids precipitation degree between organic waste that has passed through an effective resource recovery device and organic waste that has not passed through the effective resource recovery device according to an embodiment of the present invention.

FIG. 12 illustrates the organic waste (①) that has passed through the effective resource recovery device 900 and solid-liquid separated in the third solid-liquid separation tank without chemical injection, the organic wastes (②, ③, ④, ⑤, and ⑥) that have passed through the effective resource recovery device 900 and solid-liquid separated in the third solid-liquid separation tank with chemical injected, and the organic waste (⑥) separated by the conventional recovery device instead of the effective resource recovery device 900.

Referring to FIG. 12, it may be identified that stable solid-liquid separation is achieved with the degree of precipitation of the solid components being a predetermined level or more if the effective resource recovery device has been passed through regardless of whether chemicals have been injected or not, whereas the degree of precipitation of the solid components is significantly low.

Referring back to FIG. 9, the third solid-liquid separation tank 980 delivers the separated solid components to the first solid-liquid separation tank 930 so that the phosphorus component may be recovered by the phosphorus elution tank 940 and the phosphorus recovery tank 960. Meanwhile, the third solid-liquid separation tank 980 performs a denitrification process (not shown) to additionally remove the nitrogen component remaining in the liquid components from the separated liquid components and then discharges the liquid components, and delivers some of the liquid components to the phosphorus recovery tank 960 to allow the phosphorus recovery tank 960 to have a neutral pH environment.

The nitrogen recovery device 990 recovers ammonia gas degassed in the aerobic tank 970.

Figure 13:
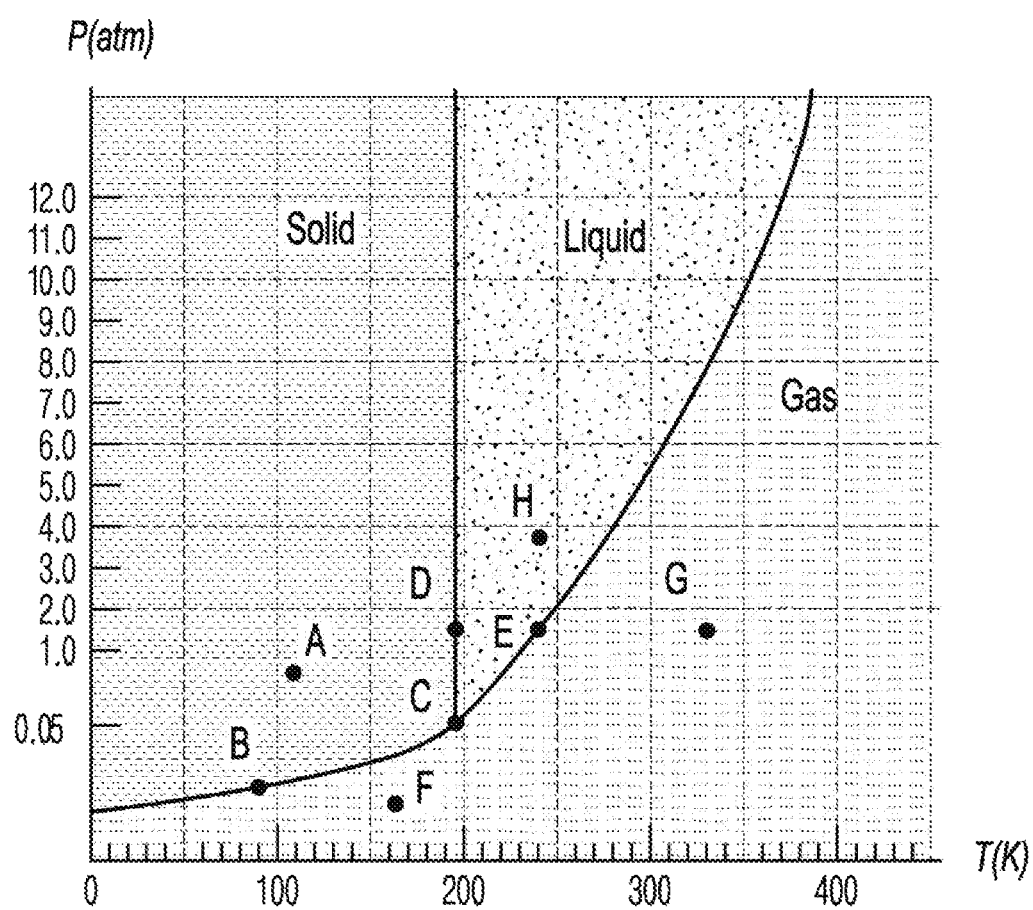
FIG. 13 is a graph illustrating a change in the state of nitrogen depending on pressures and temperatures.

The nitrogen recovery device 990 is implemented as a cooling device to recover ammonia gas as liquid ammonia water. As illustrated in FIG. 13, the ammonia gas has a different state depending on the pressure and temperature.

FIG. 13 is a graph illustrating a change in the state of nitrogen depending on pressures and temperatures.

Referring to the graph of FIG. 13, when the temperature drops to −60° C. to −40° C. in a situation where the pressure is maintained at 1 atmosphere, ammonia has a liquid phase. In this case, when the pressure increases, ammonia may have a liquid phase even at a relatively higher temperature.

Referring back to FIG. 9, the nitrogen recovery device 990 converts ammonia gas into liquid ammonia water by maintaining an appropriate pressure and temperature to recover the nitrogen component.

Meanwhile, the nitrogen recovery device 990 may obtain ammonium bicarbonate ($NH_4HCO_3$) using the carbon dioxide separated from the separation device 920. Carbon dioxide is dissolved in water. In this case, if ammonia gas is injected into the solution in which carbon dioxide is dissolved, ammonium bicarbonate is produced. The nitrogen recovery device 990 recovers the nitrogen component by recovering the so-produced ammonium bicarbonate.

As such, the effective resource recovery device 900 may minimize the use of chemicals by appropriately using by-products generated in the treatment process, thus economically recovering effective resources and may recover, without loss, most of the phosphorus component, which is mainly in a solid phase, as well as nitrogen contained in the organic waste.

The effective resource recovery devices described above with reference to FIGS. 1 to 9 may further include a purification unit (not shown) for additionally removing residual nitrogen.

Figure 16:
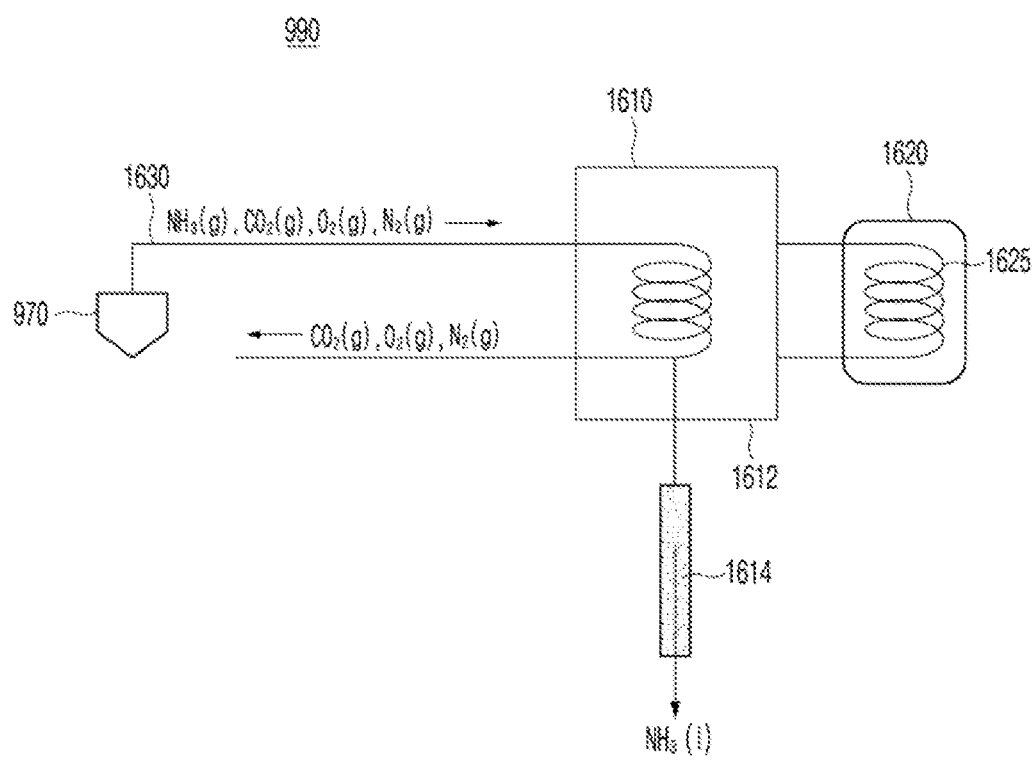
FIG. 16 is a view illustrating a configuration of a nitrogen recovery device according to a second embodiment of the present invention.
Figure 17:
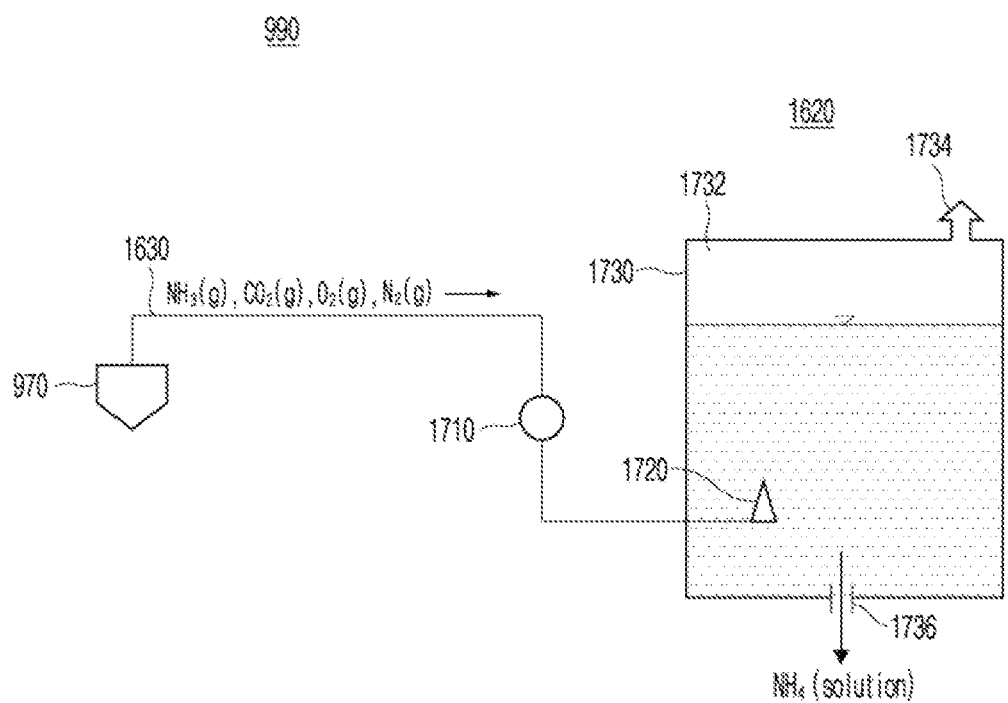
FIG. 17 is a view illustrating a configuration of a nitrogen recovery device according to a third embodiment of the present invention.

The nitrogen recovery device 990 may be configured and operated as illustrated in FIG. 17, but may otherwise recover the nitrogen component using a coolant. The nitrogen recovery device 990 is illustrated in FIGS. 15 to 17.

Figure 15:
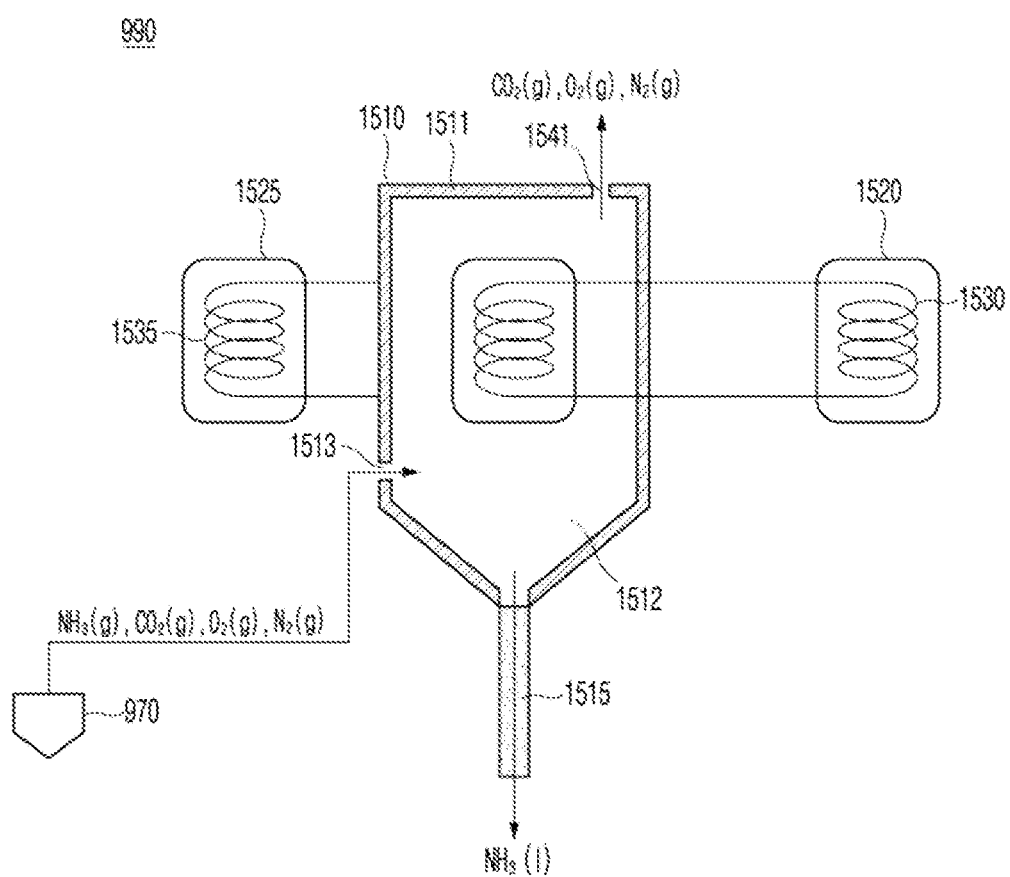
FIG. 15 is a view illustrating a configuration of a nitrogen recovery device according to a first embodiment of the present invention.

FIG. 15 is a view illustrating a configuration of a nitrogen recovery device according to the first embodiment of the present invention.

Referring to FIG. 15, a nitrogen recover device 990 includes a cooling tower 1510, coolant storage tanks 1520 and 1525, and a pipe 1530.

The aeration of the digestion liquid in the aerobic tank 970 generates several gases including $NH_3$, $CO_2$, $O_2$ and $N_2$. $CO_2$ is produced when the alkalinity of the digestion liquid is high according to the following formula.

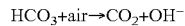

$$HCO_3 + air \rightarrow CO_2 + OH^-$$

$OH^-$ raises the pH and thus shifts the equilibrium of $NH_4^+$ to $NH_3^+$, generating Nh3gas3gas from $NH_4^+$ in the liquid. $O_2$ and $N_2$ are provided from the air. The gases generated in the aerobic tank 970 are introduced into the cooling tower 1510 through the gas inlet 713 of the cooling tower 1510.

The cooling tower 1510 is maintained at −77° C. to −33° C. The cooling water is delivered from the coolant storage tank 1520 to the inside of the cooling tower 1512 via the pipe 1530. The cooling tower 1510 is formed of stainless steel having a double-layer wall in which the space 1511 between the inner wall and the outer wall is filled with cooling water. The cooling water is delivered from the coolant storage tank 1525 to the space 1511 of the cooling tower by a pipe 1535. Accordingly, the cooling tower 1510 may be maintained at −77° C. to −33° C. by the cooling water.

The boiling point of each gas flowing into the cooling tower 1510 is −33.34° C. for $NH_3$, −78.5° C. for $CO_2$, −183° C. for $O_2$, and −195.8° C. for $N_2$. The respective melting points of $NH_3$, $CO_2$, $O_2$, and $N_2$ are −77.7° C., −78.5° C., −218.8° C. and −210° C., respectively. Therefore, when the mixed gas flows into the cooling tower that is maintained at a temperature between −77° C. and −33° C., $NH_3$ is liquefied, but all of the other gases remain gaseous. Accordingly, if the mixed gas is sent to the cooling tower 1510, $NH_3$ is liquefied which the mixed gas stays inside the cooling tower 1510. Liquefied $NH_3$ is dried by a drying agent, such as silica gel or $CaO_2$ and may be collected into a cylinder at the lower end 1515 of the cooling tower. If the internal pressure reaches a critical value, the remaining gases are discharged to the gas outlet 1514 of the cooling tower 1510.

The coolant storage tank 1520 stores coolant and cools the cooling water flowing into the pipe 1530. The coolant storage tank 1520 stores a coolant including some or all of dry ice, liquefied dry ice, and dry ice mixed with acetone. This coolant has a temperature of about −78.5° C. and cools the cooling water flowing into the coolant storage tank 1520 to have a temperature between −77° C. and −33° C. The cooling water introduced into the cooling tower 1510 lowers the temperature of the gas by heat exchange with the gas introduced into the cooling tower 1510 while raising its own temperature. After the cooling water whose temperature has risen is introduced into the coolant storage tank 1520 through the pipe 1530, the temperature of the cooling water decreases again due to heat exchange with the coolant. The cooling water maintains the internal temperature of the cooling tower 1510 to have the above-described temperature range while circulating through the pipe 1530.

Likewise, the coolant storage tank 1525 stores coolant and cools the cooling water flowing through the pipe 1535. The coolant storage tank 1525 also stores the coolant and cools the cooling water flowing into the coolant storage tank 1525 to have a temperature between −77° C. and −33° C. The cooling water circulating between the inner space 1511 of the cooling tower and the coolant storage tank 1525 through the pipe 1535 maintains the internal temperature of the cooling tower 1510 within the above-described temperature range.

The flow rate of the cooling water circulating through each of the pipes 1530 and 1535 is set so that the temperature of each coolant storage tank 1520 and 1525 and the temperature of the cooling water flowing through the internal space 1511 of the cooling tower is identical to each other. Further, the initial volume of cooling water used in the operation needs to be at least twice the volume filling all the pipes. Otherwise, it is difficult to maintain the temperature of the inside 1511 of the cooling tower. A sufficient amount of cooling water needs to be cooled in the coolant storage tank even while part of the cooling water is heat-exchanging inside the cooling tower.

FIG. 16 is a view illustrating a configuration of a nitrogen recovery device according to the second embodiment of the present invention.

Referring to FIG. 16, according to a second embodiment, a nitrogen recovery device 990 includes a cooling tower 1610, a coolant storage tank 1620, and a gas pipe 1630.

The cooling tower 1610 and the coolant storage tank 1620 perform the same operation as the cooling tower 1510 and the coolant storage tank 1520.

However, a gas pipe 1630 connected to the cooling tower 1610 does not inject gas into the cooling tower 1610 but allows the gas to simply pass through the cooling tower 1610. Among the several gases, $NH_3$ alone is liquefied while passing through the gas pipe 1630 in the above-described temperature range, and the remaining gases are discharged to the outside of the cooling tower 1610 through the gas pipe 1630. Liquefied $NH_3$ is dried by a drying agent, such as silica gel or $CaO_2$ and is then discharged to the lower end of the cooling tower 1614 by gravity.

FIG. 17 is a view illustrating a configuration of a nitrogen recovery device according to the third embodiment of the present invention.

Referring to FIG. 17, according to a third embodiment, a nitrogen recovery device 990 includes a blower 1710, a diffuser 1720, and a water tank 1730.

Unlike the nitrogen recovery devices 990 according to the first and second embodiments, the nitrogen recovery device 990 according to the third embodiment recovers the nitrogen component as an NH4 aqueous solution.

The solubility of $NH_3$ in water is 34% at 20° C. $NH_3$ in water is ionized into $NH_4^+$ by the following process.

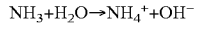

The mixed gas ($NH_3$, $CO_2$, $O_2$ and $N_2$) generated in the aerobic tank 970 is sent to the water tank 1730 via a pipe by the blower 1710, e.g., a root blower. The water tank 930 is not fully filled with water but has some empty space 1732 above the water level. This space 932 is a space for storing the gas that has passed through the water in the water tank 930. At the end of the pipe is the diffuser 1720 that diffuses the gas. The smaller the bubble of the gas entering the water, the faster the gas dissolves in the water at a given temperature.

Among the gases injected into the water tank 1730, $N_2$ is an amphoteric chemical substance that has no effect on the other gases or water, and its solubility in water at 1 bar is less than 20 mg/L. Thus, most of $N_2$ enters and exits the water without changing the properties of the water and rather quickly exits from the water, forming a pressure in the empty space 1732 formed in the water tank 1730. When a certain level of pressure is generated in the water tank 1730, $N_2$ is discharged from the water tank 1730 through the gas outlet 1734.

The solubility of $O_2$ is 40 mg/L in water at 25° C. at 1 bar and is not remarkably high. Accordingly, most of $O_2$ is also discharged through the gas outlet 1734 as is $N_2$.

$CO_2$ is another gas that comes out of the aerobic tank 970 and is injected into the water tank 1730. The solubility of $CO_2$ in water at 25° C., 1 bar is 1.45 g/L. Thus, once dissolved in water, $CO_2$ dissolves in water as follows.

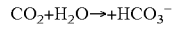

If the value of pKa is 6.367, then pH becomes 3.9 when $CO_2$ is saturated in water, so that $CO_2$ acidifies the water to help $NH_4^+$ stay in the aqueous solution.

Thus, $NH_3$ is dissolved in water and becomes $NH_4OH$ while undergoing the following process.

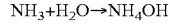

How much $NH_3$ is dissolved in water varies depending on the temperature and pH. As mentioned above, $CO_2$ is dissolved in water and the pH at ambient temperature becomes 3.9. This environment promotes the dissolution of $NH_3$ in water. Accordingly, $NH_4$ aqueous solution may be recovered at the lower end 936 of the water tank 930.

The $NH_4$ aqueous solution recovered under the following conditions in the nitrogen recovery device 990 according to the third embodiment has the following characteristics.

$NH_3$ gas is generated by aeration in water containing 2,000 mg/L of $NH_4$. After 1.5 days of aeration, 1,000 mg/L of $NH_3$ gas is generated by the aeration and sent from the aerobic tank 970 to the water tank 1730 through the pipe to be dissolved in water. The $NH_3$ gas was simply bubbled in the water using a diffuser-free pipe. Then, the density of $NH_3$ solution and the volume of $NH_4$ solution were measured to determine the density of the $NH_3$-dissolved water or $NH_4$ solution. The specific gravity of the $NH_4$ solution was 0.896 g/cc. According to the well-known relationship between a specific density and the wt % of $NH_4$ in the solution, the weight percentage of the solution of $NH_4$ was 30.48% for the solution. Currently, 30% aqueous nitrogen solution is sold as fertilizer at $350/ton. Since no chemical substances are used in the process of recovering the nitrogen aqueous solution, the $NH_4$ aqueous solution recovered by the nitrogen recovery device 990 according to the third embodiment may be certified as an organic substance.

Figure 14:
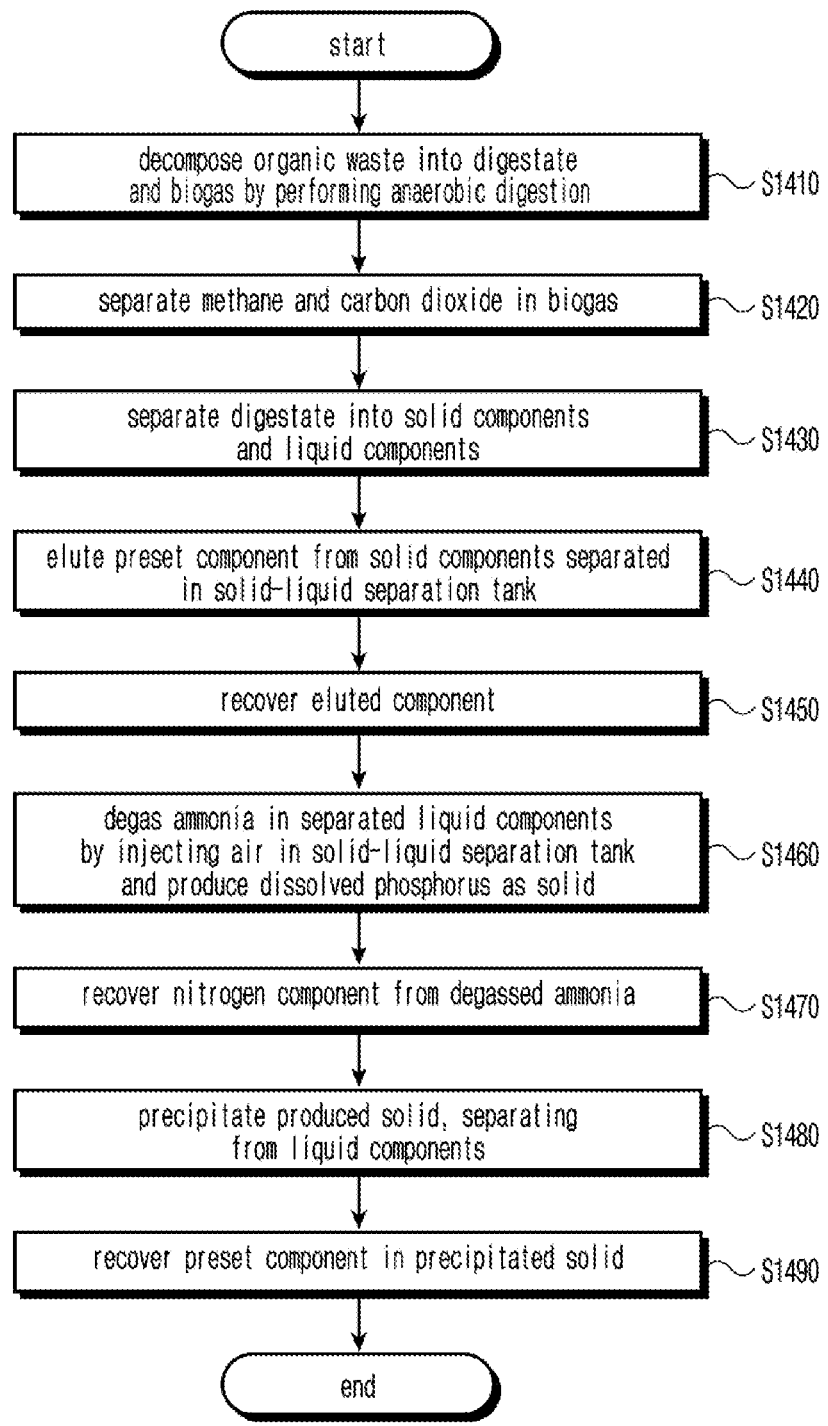
FIG. 14 is a flowchart illustrating an effective resource recovery method according to an embodiment of the present invention.

FIG. 14 is a flowchart illustrating an effective resource recovery method according to an embodiment of the present invention.

The anaerobic digester 910 decomposes organic waste into digestate and biogas by anaerobic digestion (S1410).

The separation device 920 separates methane and carbon dioxide in the biogas (S1420).

The first solid-liquid separation tank 930 separates the digestate into solid components and liquid components (S1430).

The phosphorus elution tank 940 elutes a preset component from the solid components separated in the first solid-liquid separation tank 930 (S1440).

The phosphorus recovery tank 960 recovers the eluted preset component (S1450). The preset component is eluted in the phosphorus elution tank 940, and the solid components and the liquid components are separated in the second solid-liquid separation tank 950. The phosphorus recovery tank 960 recovers the phosphorus component from the liquid components separated in the second solid-liquid separation tank 950.

The aerobic tank 970 injects air to thereby degas the dissolved ammonia from the liquid components separated in the first solid-liquid separation tank 930 and generates dissolved phosphorus into a solid (S1460).

The nitrogen recovery device 990 recovers the nitrogen component from the degassed ammonia (S1470).

The third solid-liquid separation unit 980 precipitates the generated solid components and separates them from the liquid components (S1480).

The first solid-liquid separation tank 930, the phosphorus elution tank 940, and the phosphorus recovery tank 960 recover a preset component from the precipitated solid components (S1490). The solid components precipitated by the third solid-liquid separation unit 980 are transferred to the first solid-liquid separation tank 930, and the preset component is recovered while passing through steps S630, S640 and S650 again.

Although FIGS. 7, 8, and 14 illustrate that the steps are sequentially performed, this merely provides an embodiment of the present invention. It would readily be appreciated by a skilled artisan that the steps of FIGS. 7, 8, and 14 are not limited to the order shown but may rather be performed in a different order, one or more of the steps may simultaneously be performed, or other various modifications or changes may be made thereto without departing from the scope of the present invention.

The steps or processes described above in connection with FIGS. 7, 8, and 14 may be implemented as computer-readable code in a recording medium. The computer-readable recording medium includes all types of recording devices storing data readable by a computer system. The computer-readable recording medium includes a storage medium, such as a magnetic storage medium (e.g., a ROM, a floppy disk, or a hard disk) or an optical reading medium (e.g., a CD-ROM or a DVD). Further, the computer-readable recording medium may be distributed to computer systems connected via a network, and computer-readable codes may be stored and executed in a distributed manner.

The above-described embodiments are merely examples, and it will be appreciated by one of ordinary skill in the art various changes may be made thereto without departing from the scope of the present invention. Accordingly, the embodiments set forth herein are provided for illustrative purposes, but not to limit the scope of the present invention, and should be appreciated that the scope of the present invention is not limited by the embodiments. The scope of the present invention should be construed by the following claims, and all technical spirits within equivalents thereof should be interpreted to belong to the scope of the present invention.

The invention claimed is:

1. A device for recovering a resource contained in organic waste, comprising:
   an anaerobic digester decomposing the organic waste into digestate and gases by anaerobic digestion;
   a separation device including dissolution water, the separation device receiving the gases and separating and discharging components included in the gases using a difference in gas solubility in the dissolution water;
   a first solid-liquid separation tank separating the digestate into solid components and liquid components;
   an elution tank into which only the solid components separated in the first solid-liquid separation tank are introduced, the elution tank eluting phosphorus among the introduced solid components by providing a low pH environment;
   a second solid-liquid separation tank separating the component eluted through the elution tank and remaining solid components and transferring the separated solid components to the anaerobic digester;
   a recovery tank degassing dissolved carbon dioxide in the components separated in the second solid-liquid separation tank while simultaneously performing agitation by injecting air and depositing phosphorus from the components separated in the second solid-liquid separation tank;
   an aerobic tank injecting a predetermined amount of air to thereby degas some of ammonium ions in the liquid components separated in the first solid-liquid separation tank into ammonia and generate phosphorus remaining in the liquid components into a solid;
   a nitrogen recovery tank recovering a nitrogen component from ammonia degassed in the aerobic tank; and
   a third solid-liquid separation tank separating the solid generated in the aerobic tank and the liquid components, wherein among the gases separated and discharged by the separation device, carbon dioxide is introduced into the elution tank, and wherein some of the liquid components separated in the third solid-liquid separation tank are introduced into the recovery tank.

2. The device of claim 1, wherein the third solid-liquid separation tank transfers the separated solid to the first solid-liquid separation tank.

3. The device of claim 1, wherein the nitrogen recovery tank provides a preset environment to recover the ammonia degassed in the aerobic tank in a liquid phase.

4. The device of claim 1, wherein the nitrogen recovery tank receives carbon dioxide and recovers the ammonia degassed in the aerobic tank as a solid compound.

5. A method for recovering a resource contained in organic waste, the method comprising:
   a decomposition step for decomposing the organic waste into digestate and gases by anaerobic digestion;
   a discharging step for receiving the gases and separating and discharging components included in the gases using a difference in gas solubility in the dissolution water;
   a first solid-liquid separation step for separating the digestate into solid components and liquid components;
   an elution step in which only the solid components separated in the first solid-liquid separation step are introduced, the elution step eluting phosphorus among the introduced solid components by providing a low pH environment;
   a second solid-liquid separation step for separating the component eluted in the elution step and remaining solid components and transferring the separated solid components to the decomposition step;

a deposition step for degassing dissolved carbon dioxide in the components separated in the second solid-liquid separation step while simultaneously performing agitation by injecting air and depositing phosphorus from the components separated in the second solid-liquid separation step;

a degassing step for injecting a predetermined amount of air into the liquid components separated in the first solid-liquid separation step to degas some of ammonium ions into ammonia and generate phosphorus remaining in the liquid components into a solid;

a recovery step for recovering a nitrogen component from ammonia degassed in the degassing step; and a third solid-liquid separation step for separating the solid generated through the degassing step and the liquid components, wherein among the gases discharged in the discharging step, carbon dioxide is introduced into the elution step, and wherein some of the liquid components separated in the third solid-liquid separation step are introduced into the recovery step.

6. The device of claim 1, wherein the nitrogen recovery tank maintains a preset temperature range to liquefy and recover the ammonia degassed in the aerobic tank.

7. The device of claim 1, wherein the nitrogen recovery tank maintains a preset temperature range by cooling water injected from an outside.

8. The device of claim 1, wherein the nitrogen recovery tank recovers only the ammonia degassed in the aerobic tank as aqueous solution using a difference in gas solubility in water.

9. The method of claim 5, wherein the solid separated in the third solid-liquid separation step is separated again into solid components and liquid components by the first solid-liquid separation step.

10. The method of claim 5, wherein the recovery step recovers the ammonia degassed in the degassing step, in a liquid state, by providing a preset environment.

11. The method of claim 5, wherein the recovery step receives carbon dioxide and recovers the ammonia degassed in the degassing step, in a liquid state.

12. The method of claim 5, wherein the recovery step recovers the nitrogen component from the ammonia degassed in the degassing step by maintaining a preset temperature range by cooling water injected from an outside.

13. The method of claim 1, wherein the recovery recovers only the ammonia degassed in the degassing step as aqueous solution using a difference in gas solubility in water.

* * * * *